(12) United States Patent
Levy et al.

(10) Patent No.: US 11,291,430 B2
(45) Date of Patent: Apr. 5, 2022

(54) PRECEDENT-BASED ULTRASOUND FOCUSING

(71) Applicant: INSIGHTEC, LTD., Tirat Carmel (IL)

(72) Inventors: Yoav Levy, Hinanit (IL); Eyal Zadicario, Tel Aviv-Jaffa (IL); Talia Amar, Tirat Carmel (IL)

(73) Assignee: INSIGHTEC, LTD., Tirat Carmel (IL)

( * ) Notice: Subject to any disclaimer, the term of this patent is extended or adjusted under 35 U.S.C. 154(b) by 440 days.

(21) Appl. No.: 16/314,808

(22) PCT Filed: Jul. 14, 2017

(86) PCT No.: PCT/IB2017/001029
§ 371 (c)(1),
(2) Date: Jan. 2, 2019

(87) PCT Pub. No.: WO2018/011631
PCT Pub. Date: Jan. 18, 2018

(65) Prior Publication Data
US 2019/0307427 A1 Oct. 10, 2019

Related U.S. Application Data

(60) Provisional application No. 62/362,151, filed on Jul. 14, 2016.

(51) Int. Cl.
| | |
|---|---|
| *A61B 8/08* | (2006.01) |
| *A61B 6/00* | (2006.01) |
| *A61B 8/00* | (2006.01) |
| *A61B 90/00* | (2016.01) |
| *A61B 6/03* | (2006.01) |

(Continued)

(52) U.S. Cl.
CPC .......... *A61B 8/5269* (2013.01); *A61B 6/5217* (2013.01); *A61B 8/0808* (2013.01);
(Continued)

(58) Field of Classification Search
CPC ....... A61B 8/5269; A61B 8/00; A61B 8/4416; A61B 8/54; A61B 8/58; G01S 15/8927;
(Continued)

(56) References Cited

U.S. PATENT DOCUMENTS

| | | | | |
|---|---|---|---|---|
| 6,027,447 A | * | 2/2000 | Li | ........................ G01S 7/52049 600/447 |
| 6,120,450 A | * | 9/2000 | Li | ........................ G01S 15/8927 600/447 |

(Continued)

FOREIGN PATENT DOCUMENTS

WO 2011027264 A1 2/2011

OTHER PUBLICATIONS

Written Opinion of the International Searching Authority for International Application No. PCT/IB2017/001029, dated Dec. 12, 2018, 10 pages.

*Primary Examiner* — Amelie R Davis
(74) *Attorney, Agent, or Firm* — Morgan, Lewis & Bockius LLP

(57) ABSTRACT

Various approaches for operating an ultrasound transducer having multiple transducer elements include acquiring one or more measurements of anatomical regions through which ultrasound waves emitted from the transducer elements travel; for each of the anatomical regions, determining values of characteristics based at least in part on the measurement(s); computationally predicting aberrations of the ultrasound waves traveling through the anatomical regions by using the first values as input to a predictor that has been computationally trained to predict ultrasound aberrations based on values of the characteristics; and driving the transducer elements to compensate for the predicted aberrations.

39 Claims, 22 Drawing Sheets

(51) Int. Cl.
  *G06N 3/02* (2006.01)
  *G06N 20/00* (2019.01)
(52) U.S. Cl.
  CPC .......... *A61B 8/4416* (2013.01); *A61B 8/4488* (2013.01); *A61B 8/5246* (2013.01); *A61B 8/5253* (2013.01); *A61B 8/5261* (2013.01); *A61B 8/54* (2013.01); *A61B 8/58* (2013.01); *A61B 6/032* (2013.01); *A61B 6/037* (2013.01); *A61B 8/0875* (2013.01); *A61B 8/4245* (2013.01); *A61B 2090/374* (2016.02); *G06N 3/02* (2013.01); *G06N 20/00* (2019.01); *G06T 2207/20081* (2013.01); *G06T 2207/20084* (2013.01)

(58) Field of Classification Search
  CPC ....................... G06N 3/02; G06N 20/00; G06T 2207/20084; G06T 2207/20081
  See application file for complete search history.

(56) References Cited

U.S. PATENT DOCUMENTS

| | | | | |
|---|---|---|---|---|
| 6,364,835 | B1* | 4/2002 | Hossack | G01S 7/52034 600/443 |
| 2004/0006272 | A1* | 1/2004 | Vortman | A61B 8/0816 600/443 |
| 2004/0122323 | A1 | 6/2004 | Vortman et al. | |
| 2007/0078347 | A1* | 4/2007 | Srinivasan | G01S 15/8979 600/465 |
| 2007/0167781 | A1* | 7/2007 | Vortman | G01S 7/52019 600/443 |
| 2010/0158332 | A1* | 6/2010 | Rico | A61B 8/5223 382/128 |
| 2011/0270136 | A1 | 11/2011 | Vitek et al. | |
| 2012/0020530 | A1* | 1/2012 | Yu | G06T 5/003 382/107 |
| 2012/0108968 | A1* | 5/2012 | Freiburger | A61B 8/0825 600/443 |
| 2012/0128223 | A1* | 5/2012 | Rivaz | A61B 8/485 382/131 |
| 2012/0136255 | A1* | 5/2012 | Fan | A61B 8/0833 600/443 |
| 2013/0144165 | A1* | 6/2013 | Ebbini | G01S 7/52046 600/439 |
| 2014/0350439 | A1 | 11/2014 | Zur et al. | |
| 2015/0359512 | A1* | 12/2015 | Boctor | A61B 8/469 600/444 |
| 2016/0012582 | A1* | 1/2016 | Mauldin, Jr. | G06T 11/60 382/131 |

* cited by examiner

SLICES:
- XZ THROUGH COM x 3
- 3 XZ SLICES, 5mm APART.
- 3 XZ SLICES, 2mm APART, PARTIAL Z RANGE.
- XZ, YZ AND CYLINDER OF RADIUS 5mm, FULL AND PARTIAL Z RANGE.

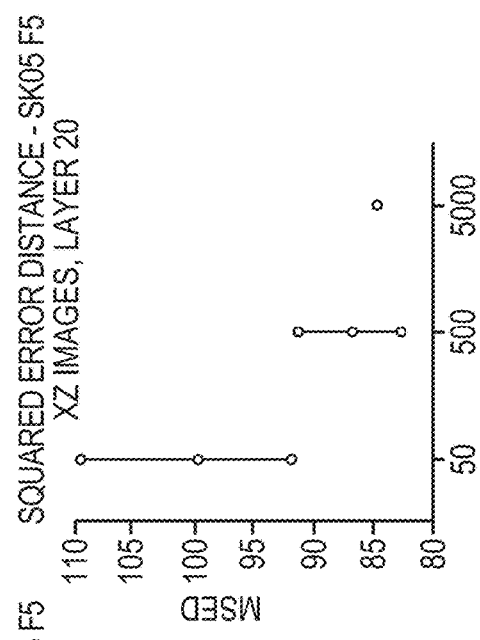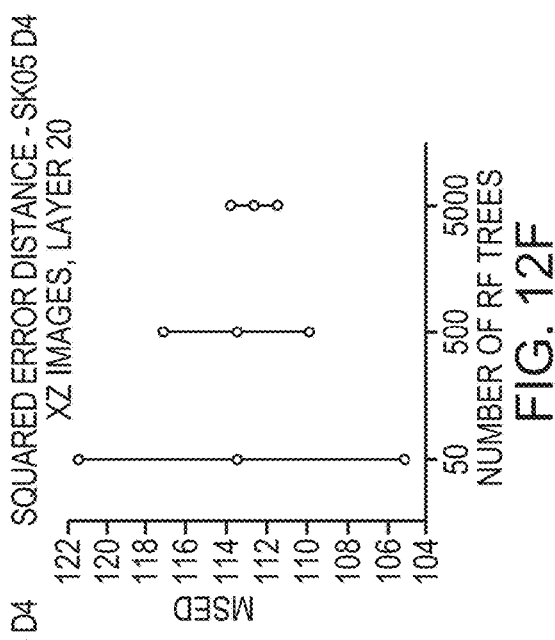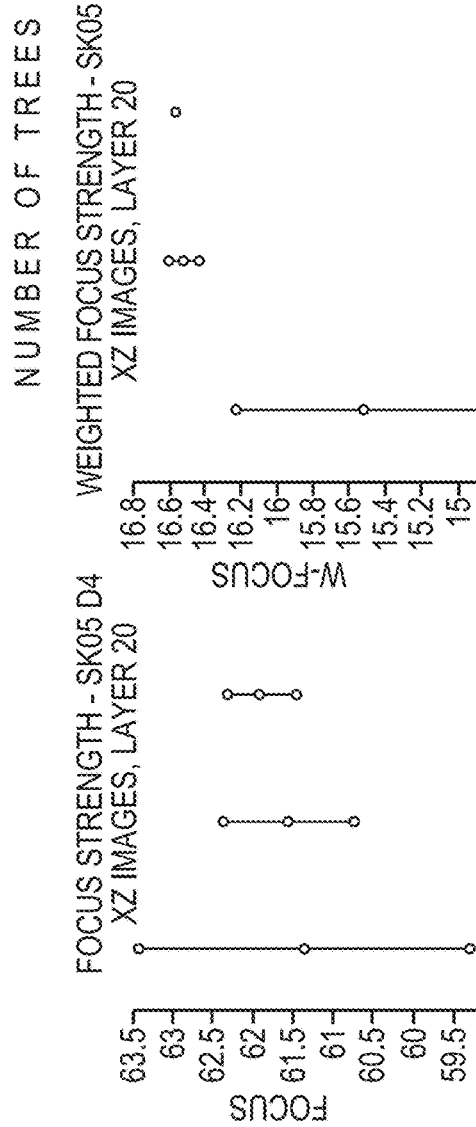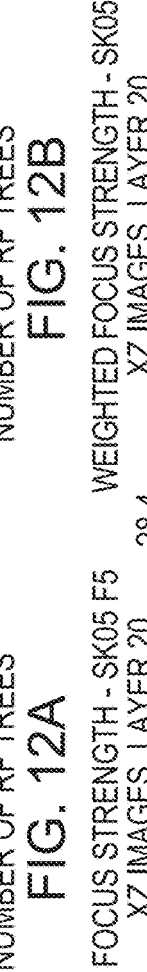
FIG. 12A  FIG. 12B  FIG. 12C  FIG. 12D  FIG. 12E  FIG. 12F

PRECEDENT-BASED ULTRASOUND FOCUSING

CROSS-REFERENCE TO RELATED APPLICATION

This application is a U.S. National Phase Application of PCT/IB2017/001029, filed Jul. 14, 2017, which claims the benefit of and priority to U.S. Provisional Patent Application No. 62/362,151, filed Jul. 14, 2016. The foregoing applications are incorporated herein by reference in their entireties.

FIELD OF THE INVENTION

The present invention relates, generally, to ultrasound focusing and, more particularly, to precedent-based ultrasound focusing techniques.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, thereby eliminating the need for invasive surgery, targeted drug delivery, control of the blood-brain barrier, lysing of clots, and other surgical procedures. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MM) may be used to visualize the patient and target, and thereby to guide the ultrasound beam.

As acoustic energy passes through tissue, it may interact with the tissue through multiple processes, including propagation, scattering, absorption, reflection, and refraction. The intensity of the acoustic energy reaching the target generally determines the therapeutic effectiveness of the treatment, i.e., the volume of tissue destroyed in the vicinity of the focal zone. The size of the focal zone may also depend upon system parameters such as transducer element characteristics, frequency of the acoustic energy, and focal depth (the distance from the transducer to the focal zone), as well as patient-related parameters, such as tissue inhomogeneity.

When a transducer is activated, the relative phases of drive signals delivered to each transducer element may be adjusted based on the distance of each transducer element from the focal zone. Generally, an average speed of sound is used to approximate the speed at which the acoustic energy passes through tissue and to predict the location of the focal zone.

While system parameters are generally fixed for a given transducer array, tissue homogeneity may vary significantly from patient to patient, and even between different tissue regions within the same patient. Tissue inhomogeneity may decrease the intensity of the acoustic energy reaching the focal zone and may even move the location of the focal zone within the patient's body. Specifically, because the speed of sound differs in different types of tissue, as portions of a beam of acoustic energy travel along different paths having different tissue types towards the focal zone, they may experience different speeds of sound, which may shift the relative phases of acoustic energy transmitted from respective transducer elements. This phase shifting may decrease the constructive interference of the acoustic energy at the focal zone, which may reduce the effectiveness of the treatment, or may even move the focal zone in a manner difficult to predict.

Tissue inhomogeneity may also cause refraction of acoustic energy at the boundaries of tissue regions having different speeds of sound. Refraction may decrease constructive interference, and hence, the intensity of the acoustic energy at the focal zone, particularly when the acoustic energy passes through bone. Thus, inhomogeneous tissue structures may generate beam aberrations and refractions, which may distort the focus and reduce the intensity, thus affecting treatment efficiency. Further, in ultrasound imaging, tissue inhomogeneity may result in an inhomogeneous distribution of the acoustic velocity across the pulse wavefront. When parts of the pulse wavefront travel faster (or slower) than other parts, a certain amount of error in time delays and/or intensities of received echo signals may occur in some ultrasound channels. This becomes a source of image degradation in ultrasound beamforming.

Accordingly, there is a need for an approach that predicts and accounts for aberrations of the ultrasound beam when traversing inhomogeneous tissue.

SUMMARY

The present invention provides systems and methods for predicting the effects on an ultrasound beam (e.g., aberrations) when traversing tissue (such as a human skull) having a complex structure, shape, density, and/or thickness using a precedent-based approach. In various embodiments, an acquired training set (or a library) including various features of the tissue (e.g., a skull) and acoustic aberrations (e.g., phase shifts, time delays, intensities, etc.) resulting from travel of an acoustic beam through the tissue is first created. The tissue features may be obtained using an imaging modality or a combination of imaging modalities and/or extracted using a neural network as further described below; the aberrations may be measured using a sensor (e.g., a hydrophone). A relationship between observed tissue features and the measured aberrations can be determined using, for example, by training the neural network (or other machine learning process) using the training set of images. After training, the acoustic aberrations associated with an image of the tissue of a new patient may be predicted using the trained neural network. In one implementation, the parameter (e.g., the phase) or parameters assigned to each of the transducer elements of a phased-array ultrasound system can then be adjusted based on the predicted aberration (e.g., phase shift) to compensate for the acoustic aberrations expected to be caused by the tissue, thereby improving focusing properties at the target region. In another embodiment, information (e.g., time delays and/or intensities) associated with ultrasound signals reflected from a target region is adjusted based on the predicted aberrations for improving the quality of ultrasound imaging.

Accordingly, in one aspect, the invention pertains to a method of operating an ultrasound transducer having multiple transducer elements. In various embodiments, the method includes (a) acquiring the first series of one or more measurements of multiple first anatomical regions through which ultrasound waves emitted from the transducer elements will travel; (b) for each of the first anatomical regions, determining the first values of multiple characteristics (e.g., structures, shapes, densities and/or thickness of the first anatomical regions) based at least in part on the first series of measurements; (c) computationally predicting the first aberrations of the ultrasound waves traveling through the first anatomical regions by using the first values as input to a predictor that has been computationally trained to predict ultrasound aberrations based on the values of the characteristics; and (d) driving the transducer elements to compensate for the predicted first aberrations. In one implementation, the method further includes computationally predicting the reliability of the predicted first aberrations. In addition, the measurements may include data obtained from the images of the first anatomical regions, acoustic reflections from the first anatomical regions, and/or acoustic spectral activities at the first anatomical regions.

In some embodiments, the characteristics include anatomical characteristics, sonication parameters, information of the transducer elements, and/or characteristics of a measurement system. For example, the sonication parameters may include a frequency, an intensity and/or a phase associated with each one of the ultrasound waves. The information of the transducer elements may include a size, a shape, a location and/or an orientation of each transducer element. In one embodiment, the information is extracted by transfer learning, autoencoding, principal component analysis and/or scale-invariant feature transform. In addition, the characteristics may further include the ultrasound aberrations predicted using a model. In various embodiments, the first aberrations include phase shifts, time delays, and/or changes in intensities associated with the transducer elements and/or the shape distortion of a focus generated by the ultrasound waves. One or more of the first anatomical regions may be traversed by a beam emitted by one or more of the transducer elements.

The method may include computationally training the predictor using the second series of one or more measurements of each of multiple second anatomical regions (different from the first anatomical regions or overlapping with the first anatomical regions), the second values of multiple characteristics associated with the second anatomical regions, and the second ultrasound aberrations associated with the second values of the characteristics. The computational prediction step may include using the predictor to predict the first aberrations based at least in part on similarities between the first values of the characteristics associated with the first anatomical regions and the second values of the characteristics associated with the second anatomical regions. In one embodiment, the similarity is determined based at least in part on pointwise similarity between the first and second series of measurements. In addition, the second ultrasound aberrations are acquired using an aberration measurement and/or an aberration prediction. In some embodiments, one or more of the second values of the characteristics associated with the second anatomical regions are redundant. The second series of measurements may include two or more redundant values that correspond to different second ultrasound aberrations and/or different preprocessing.

In various embodiments, the predictor predicts the first aberrations based on a relationship between the second values of the characteristics associated with the second anatomical regions and the second ultrasound aberrations associated with the second values of the characteristics using a machine learning process. The relationship may be determined using regression and/or classification. In addition, the second ultrasound aberrations may include phase shifts having real components and imaginary components; the regression and/or classification may be separately performed on the real and imaginary components.

The method may include preprocessing the first and/or second series of measurements prior to determining the first and/or second values of the characteristics, respectively. Preprocessing the first and/or second series of measurements may be carried out in multiple steps; one or more of the steps used to preprocess the first series of measurements may be the same as one or more of the steps used to preprocess the second series of measurements. In addition, the second series of measurements may include data derived from the second series of images of the second anatomical regions, and the preprocessing may include determining rotation angles of the second series of images of the second anatomical regions prior to determining characteristics thereof. In some embodiments, the method includes acquiring the third series of images of the second anatomical regions based at least in part on the determined rotation angles. The third series of images of the second anatomical regions is acquired using resampling and/or interpolation of the second series of images of the second anatomical regions.

The method may include removing bias in the second ultrasound aberrations. In addition, the method may include preprocessing the second ultrasound aberrations based at least in part on estimation of a relative bias in the second ultrasound aberrations using a physical model and removing the relative bias in the second ultrasound aberrations. In some embodiments, the method includes manipulating one or more of the second ultrasound aberrations. The manipulation includes unwrapping, scaling to a uniform ultrasound transmission frequency, and/or computational adjustment of a measurement location to the second measurement location. In addition, the predictor may include a neural network. In one embodiment, the characteristics of the first anatomical regions are determined based at least in part on angles between orientations of the first anatomical regions and beam paths of the ultrasound waves traveling therethrough. In addition, the method may further include determining the accuracy of the predicted first aberrations of the ultrasound waves based on a reliability estimation of the prediction, a similarity measure between the first series and a second series of measurements, and/or a prediction success associated with the second series of measurements.

In another aspect, the invention relates to an ultrasound system including an ultrasound transducer having multiple transducer elements; a measuring system for acquiring the first series of measurements of multiple first anatomical regions through which the ultrasound waves emitted from the transducer elements will travel; and a processor. In various embodiments, the processor is configured to determine the first values of multiple characteristics (e.g., structures, shapes, densities and/or thickness of the first anatomical regions) based at least in part on the measurements; execute a predictor that has been computationally trained to predict ultrasound aberrations based on values of the characteristics; use the first values as input to the executing predictor so as to allow the predictor to predict the first aberrations of the ultrasound waves traveling through the first anatomical regions; and drive the transducer elements to compensate for the predicted aberrations. In one implementation, the processor is further configured to computationally predict the reliability of the predicted first aberrations. In addition, the measuring system may include an imager for acquiring the first series of images of the first anatomical regions and/or an acoustic detector for detecting acoustic reflections from the first anatomical regions and/or acoustic spectral activities at the first anatomical regions. In one embodiment, the imager includes a magnetic resonance imaging device, a computer tomography device, a positron emission tomography device, a single-photon emission computed tomography device, and/or an ultrasonography device.

In some embodiments, the characteristics include anatomical characteristics, sonication parameters, information of the transducer elements, and/or characteristics of the measuring system. For example, the sonication parameters may include a frequency, an intensity and/or a phase associated with each one of the ultrasound waves. The information of the transducer elements may include a size, a shape, a location and/or an orientation of each transducer element. In one embodiment, the information is extracted by transfer learning, autoencoding, principal component analysis and/or scale-invariant feature transform. In addition, the characteristics may further include the ultrasound aberrations predicted using a model. In various embodiments, the first aberrations include phase shifts, time delays, and/or changes in intensities associated with the transducer elements and/or the shape distortion of a focus generated by the ultrasound waves. One or more of the first anatomical regions may be traversed by a beam emitted by one or more of the transducer elements.

The processor may be further configured to computationally train the predictor using the second series of measurements of multiple second anatomical regions (different from the first anatomical regions or overlapping with the first anatomical regions), the second values of multiple characteristics associated with the second anatomical regions, and the second ultrasound aberrations associated with the second values of the characteristics. The processor may be configured to use the predictor to predict the first aberrations based at least in part on similarities between the first values of the characteristics associated with the first anatomical regions and the second values of the characteristics associated with the second anatomical regions. In one embodiment, the similarity is determined based at least in part on pointwise similarity between the first and second series of measurements. In addition, the processor may be configured to predict the second values of the characteristics associated with the second anatomical regions using an aberration measurement and/or an aberration prediction. In some embodiments, one or more of the second values of the characteristics associated with the second anatomical regions are redundant. The second series of measurements may include two or more redundant values that correspond to different second ultrasound aberrations and/or different preprocessing.

In various embodiments, the predictor predicts the first aberrations based on a relationship between the second values of the characteristics associated with the second anatomical regions and the second ultrasound aberrations associated with the second values of the characteristics using a machine learning process. The relationship may be determined using regression and/or classification. In addition, the second ultrasound aberrations may include phase shifts having real components and imaginary components; the regression and/or classification may be separately performed on the real and imaginary components.

The processor may be configured to preprocess the first and/or second series of measurements prior to determining the first and/or second values of the characteristics, respectively. Preprocessing the first and/or second series of measurements may be carried out in multiple steps; one or more of the steps used to preprocess the first series of measurements may be the same as one or more of the steps used to preprocess the second series of measurements. In addition, the second series of measurements may include data derived from the second series of images of the second anatomical regions, and preprocessing may include determining rotation angles of the second series of images of the second anatomical regions prior to determining characteristics thereof. In some embodiments, the processor is further configured to acquire the third series of images of the second anatomical regions based at least in part on the determined rotation angles. The processor may be further configured to acquire the third series of images of the second anatomical regions using resampling and/or interpolation of the second series of images of the second anatomical regions.

The processor may be further configured to remove bias in the second ultrasound aberrations. In addition, the processor may be configured to preprocessing the second ultrasound aberrations based at least in part on estimation of a relative bias in the second ultrasound aberrations using a physical model and remove the relative bias in the second ultrasound aberrations. In some embodiments, the processor is configured to manipulate one or more of the second ultrasound aberrations. The manipulation includes unwrapping, scaling to a uniform ultrasound transmission frequency, and/or computational adjustment of a measurement location to the second measurement location. In addition, the predictor may include a neural network. In one embodiment, the processor is configured to determine the characteristics of the first anatomical regions based at least in part on angles between orientations of the first anatomical regions and beam paths of the ultrasound waves traveling therethrough. In addition, the processor may be further configured to determine the accuracy of the predicted first aberrations of the ultrasound waves based on a reliability estimation of the prediction, a similarity measure between the first series and a second series of measurements, and/or a prediction success associated with the second series of measurements.

Another aspect of the invention relates to a method of operating an ultrasound transducer having multiple transducer elements. In various embodiments, the method includes (a) acquiring the first series of one or more measurements of multiple anatomical regions through which ultrasound waves emitted from the transducer elements travel; (b) for each of the anatomical regions, determining values of multiple characteristics based at least in part on the first series of measurements; (c) computationally predicting an intensity of the ultrasound waves at a target region after traveling through the anatomical regions by using the values as input to a predictor that has been computationally trained to predict an ultrasound intensity at the target region based on values of the characteristics; and (d) based at least in part on the predicted ultrasound intensity, driving the transducer elements to generate a desired ultrasound focus at the target region. In one implementation, the method further includes determining the accuracy of the predicted intensity of the ultrasound waves based on a reliability estimation of the prediction, a similarity measure between the first series and the second series of measurements, and/or a prediction success associated with the second series of measurements.

In yet another aspect, an ultrasound system includes an ultrasound transducer having multiple transducer elements; a measuring system for acquiring one or more measurements of multiple anatomical regions through which the ultrasound waves emitted from the transducer elements will travel; and a processor (which may be one or more microprocessors, a multicore processor, a distributed processor architecture, etc.). In various embodiments, the processor is configured to determine values of multiple characteristics based at least in part on the measurements; execute a predictor that has been computationally trained to predict an ultrasound intensity at a target region based on values of the characteristics; use the values as input to the executing predictor so as to allow the predictor to predict an intensity of the ultrasound waves at the target region after traveling through the anatomical regions; and drive the transducer elements to generate a desired ultrasound focus at the target region. In one implementation, the measuring system includes an imager having a magnetic resonance imaging device, a computer tomography device, a positron emission tomography device, a single-photon emission computed tomography device, and/or an ultrasonography device.

Still another aspect of the invention relates to a method of predicting a likelihood of ultrasound treatment success using the first measurement setup. In various embodiments, the method includes (a) acquiring the first series of one or more measurements of multiple anatomical regions through which ultrasound waves emitted from the transducer elements travel; (b) for each of the anatomical regions, determining values of multiple characteristics based at least in part on the first series measurements; (c) computationally predicting a treatment value (e.g., a maximal temperature at the target region, a shape distortion of a focus generated by the ultrasound waves, a required acoustic energy for achieving a predefined temperature, and/or a required temperature for successful treatment) associated with the ultrasound waves at a target region after traveling through the anatomical regions by using the values of the characteristics as input to a predictor that has been computationally trained to predict a treatment value associated with the ultrasound waves at the target region based on values of the characteristics; and (d) based at least in part on the predicted treatment value, computationally predicting the likelihood of ultrasound treatment success.

In various embodiments, the characteristics include anatomical characteristics, sonication parameters, information of the transducer elements, characteristics of a measurement system, predicted intensities associated with the transducer elements at the target region using a prediction model, and/or a reliability of predicted aberrations of the ultrasound waves traveling through the anatomical regions. In addition, the method may include selecting the second measurement setup and computationally predicting a likelihood of ultrasound treatment success using the second measurement setup. The measurement setup may include a transducer location, a transducer frequency and/or a transducer orientation with respect to a location of the target region. In some embodiments, the method further includes selecting an optimal measurement setup. In addition, the method may include determining the accuracy of the predicted treatment value associated with the ultrasound waves based on a reliability estimation of the prediction, a similarity measure of the first series and the second series of measurements, and/or a prediction success associated with the second measurements.

In another aspect, the invention relates to a method of operating an ultrasound transducer having multiple transducer elements. In various embodiments, the method includes (a) acquiring a series of one or more measurements of multiple anatomical regions through which ultrasound waves emitted from the transducer elements will travel; (b) for each of the anatomical regions, determining the values of multiple characteristics based at least in part on the series of measurements; (c) computationally predicting the aberrations of the ultrasound waves traveling through the anatomical regions by using the values as input to a predictor that has been computationally trained to predict ultrasound aberrations based on the values of the characteristics; (d) driving the transducer elements to acquire one or more image of a target region; and (e) processing the acquired image(s) to compensate for the predicted first aberrations.

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which:

FIGS. 12A-12F illustrate the relationship between the degree to which predictions deviate from actual measurements and the number of trees used in a random-forest model.

DETAILED DESCRIPTION

Figure 1A:
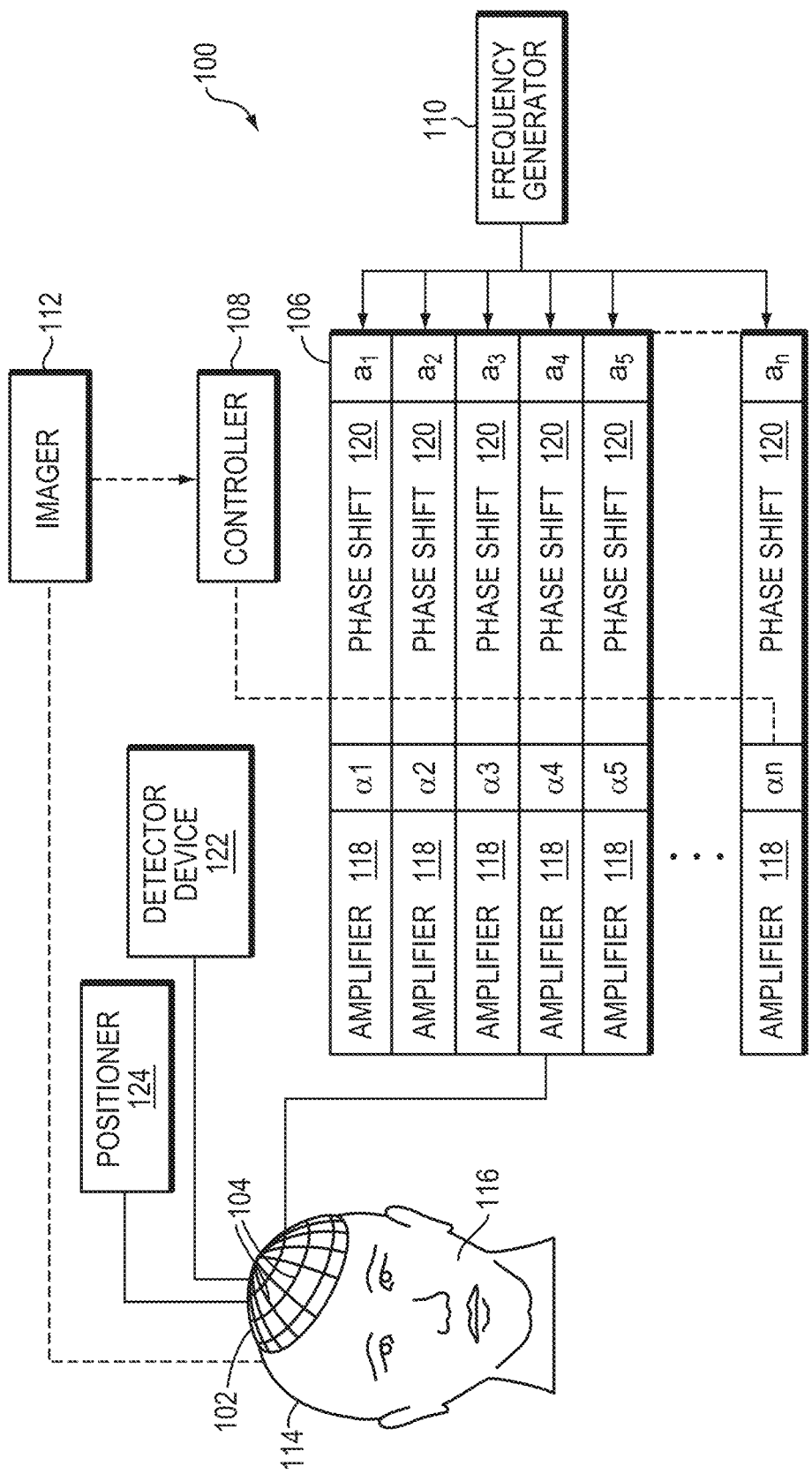
FIG. 1 illustrates a focused ultrasound system in accordance with various embodiments.

FIG. 1 illustrates an exemplary ultrasound therapy system 100 for focusing ultrasound onto a target region 101 within a patient's brain through the skull. One of ordinary skill in the art, however, will understand that the ultrasound system 100 described herein may be applied to any part of the human body. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes an imager 112, such as a magnetic resonance imaging (MM) device, a computer tomography (CT) device, a positron emission tomography (PET) device, a single-photon emission computed tomography (SPECT) device, an optical camera or an ultrasonography device, for acquiring information of the target region 101 and its surrounding region and/or determining anatomical characteristics of the skull 114 of a patient's head 116.

The array 102 may have a curved (e.g., spherical or parabolic) shape suitable for placement near the surface of the skull 114 or a body part other than the skull, or may include one or more planar or otherwise shaped sections. Its dimensions may vary, depending on the application, between millimeters and tens of centimeters. The transducer elements 104 of the array 102 may be piezoelectric ceramic elements or silicon-based elements, and may be mounted in any material suitable for damping the mechanical coupling between the elements 104. Piezo-composite materials, or generally any materials (e.g., silicon devices) capable of converting electrical energy to acoustic energy, may also be used. To assure maximum power transfer to the transducer elements 104 and minimal reflections, the elements 104 may be configured for a specific (i.e., matching) electrical impedance (e.g., 50Ω).

The transducer array 102 is coupled to the beamformer 106, which drives the individual transducer elements 104 so that they collectively produce a focused ultrasonic beam or field at the target region 101. For n transducer elements, the beamformer 106 may contain n driver circuits, each including or consisting of an amplifier 118 and a phase delay circuit 120; drive circuit drives one of the transducer elements 104. The beamformer 106 receives a radio frequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In various embodiments, the frequency generator 110 is integrated with the beamformer 106. The radio frequency generator 110 and the beamformer 106 are configured to drive the individual transducer elements 104 of the transducer array 102 at the same frequency, but at of different phases and/or different amplitudes. In some embodiments, the transducer array 102 is divided into multiple sub-regions each including a one- or two-dimensional array (i.e., a row or a matrix) of transducer elements 104. The sub-regions may be separately controllable, i.e., they are each capable of emitting ultrasound waves at amplitudes, frequencies, and/or phases that are independent of the amplitudes, frequencies and/or phases of the other sub-regions.

The amplification or attenuation factors $\alpha_1$-$\alpha_n$ and the phase shifts $a_1$-$a_n$ imposed by the beamformer 106 serve to transmit and focus ultrasonic energy through the patient's skull 114 onto the target region 101, and account for wave distortions induced in the skull 114 and soft brain tissue. The amplification factors and phase shifts are computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus or any other desired spatial field patterns. In certain embodiments, the computation is based on detailed information about the characteristics (e.g., structure, thickness, density, etc.) of the skull 114 and their effects on propagation of acoustic energy. Such information may be obtained from the imaging system 112 as further described below. Image acquisition may be three-dimensional or, alternatively, the imaging system 112 may provide a set of two-dimensional images suitable for reconstructing a three-dimensional image of the skull 114 from which the anatomical characteristics (e.g., thicknesses and densities) can be inferred. Image-manipulation functionality may be implemented in the imaging system 112, in the controller 108, or in a separate device.

System 100 may be modified in various ways within the scope of the invention. For example, for diagnostic applications, the system may further include a detector device 122 that measures transmitted or reflected ultrasound from the target and/or non-target region, and which may provide the signals it receives to the controller 108 for further processing. The reflection and transmission signals may also be used as feedback for the phase and amplitude adjustments of the beamformer 106. The system 100 may contain a positioner 124 for arranging the array 102 of transducer elements 104 with respect to the patient's skull 114. In order to apply ultrasound therapy to body parts other than the brain, the transducer array 102 may take a different, e.g., a cylindrical, shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

Thus, in an ultrasound phased-array transducer, each transducer element is driven with a phase that is determined based on, for example, the location of the transducer element and the target region as well as acoustic properties of media located between the transducer element and the target region. The objective is to cause the beams from all active transducers to converge in phase at the focus. Because the acoustic properties of the bone tissue (e.g., a skull) are significantly different from those of the soft tissue, the presence of the bone tissue along the beam path may result in significant aberrations (e.g., phase shifts and/or time delays) to the acoustic beam. Approaches in the present invention compensate for these phase shifts by first predicting the phase shifts resulting from the skull using data in a training set and based on the predicted values, adjusting the phase associated with each transducer element. Approaches in the present invention may also compensate for the time delays and/or changes in intensities associated with ultrasound signals reflected from a target region for improving the imaging quality thereof.

In various embodiments, the acoustic intensity in the target of the beams after travelling through a patient's skull is predicted using a suitable learning model and/or physical model. The input from the learning model and/or physical model may include various features of the skull and/or other intervening tissue located between the transducer elements 104 and the target, and may also include the aberrations (e.g., phase shifts) predicted using any suitable learning model and/or physical model as described below. In addition, the reliability of the phase shift prediction may also be predicted using a suitable learning/physical model or extracted from a phase shift predictor (e.g., from the degree of prediction certainty). Based on the predicted acoustic intensity and phase prediction reliability for all elements in a new case study (e.g., corresponding to a single phased array with a specific treatment configuration for a specific patient), the treatment effectiveness and/or an expected maximal temperature at the target may be determined. Additionally or alternatively, the probability of focal shape distortion can be analyzed. The likelihood of successful treatment can be determined by comparing the predicted maximal temperature to a prediction of the required temperature for effective treatment. In one embodiment, the required temperature for effective treatment is predicted using a learning model trained on a training set of the tissue characteristics and treatment related features (e.g., a focal site, a mean skull thickness, a mean SDR, a maximal temperature reached, etc.) associated with a binary result of whether the treatment is successful. In various embodiments, the relative locations of the transducer and skull are adjusted, and the treatment effectiveness and/or expected maximal temperature associated with the adjusted locations are predicted as described above. This procedure is iteratively performed until the optimal treatment effectiveness and/or temperature at the target region is found.

In various embodiments, each measurement (e.g., activation of 1000 transducer elements once) may be used as a single case study and analyzed to learn a "global" property (e.g., a characteristic, such as a size, a location and/or a temperature) of the beam focus and/or treatment effectiveness. In one embodiment, a 2D matrix in which one dimension represents the transducer elements and another dimension represents the characteristics associated with the element and/or its corresponding skull patch (e.g., element location, skull thickness, skull density, incident angle of the beam, a predicted amplitude in the target, a predicted phase-prediction reliability, etc.) may be created. The elements may be ordered by their locations (e.g., if the transducer elements occupy a half of a sphere, they can be arranged as a spiral) for increasing convolution effectiveness. The 2D matrix may then be provided to a convolutional layer in one dimension (to relate the features associated with each element separately without pooling, or to relate the elements) or to a convolutional layer in two dimensions with or without pooling in the dimension of the transducer elements. Additional features (e.g., a frequency, a spectral activity, etc.) may be added as well.

Another embodiment may use as an input "image" a matrix having more than two dimensions. For example, a 32×32 matrix may be used to represent image data from 1024 elements in a transducer of a half-spherical shape that is projected onto a plane (e.g. of maximal symmetry) and organized in the matrix by the elements' spatial location within the projection plane. The skull features used to train the model correspond to another dimension, so that if we have 40 features (e.g., thickness, angles, element location) per element, the input matrix for each image has a size of 40×32×32. In addition, using outputs from parallel layers later to be concatenated may enable the features that are measurement-dependent and/or constant for all elements to be included.

Figure 2:
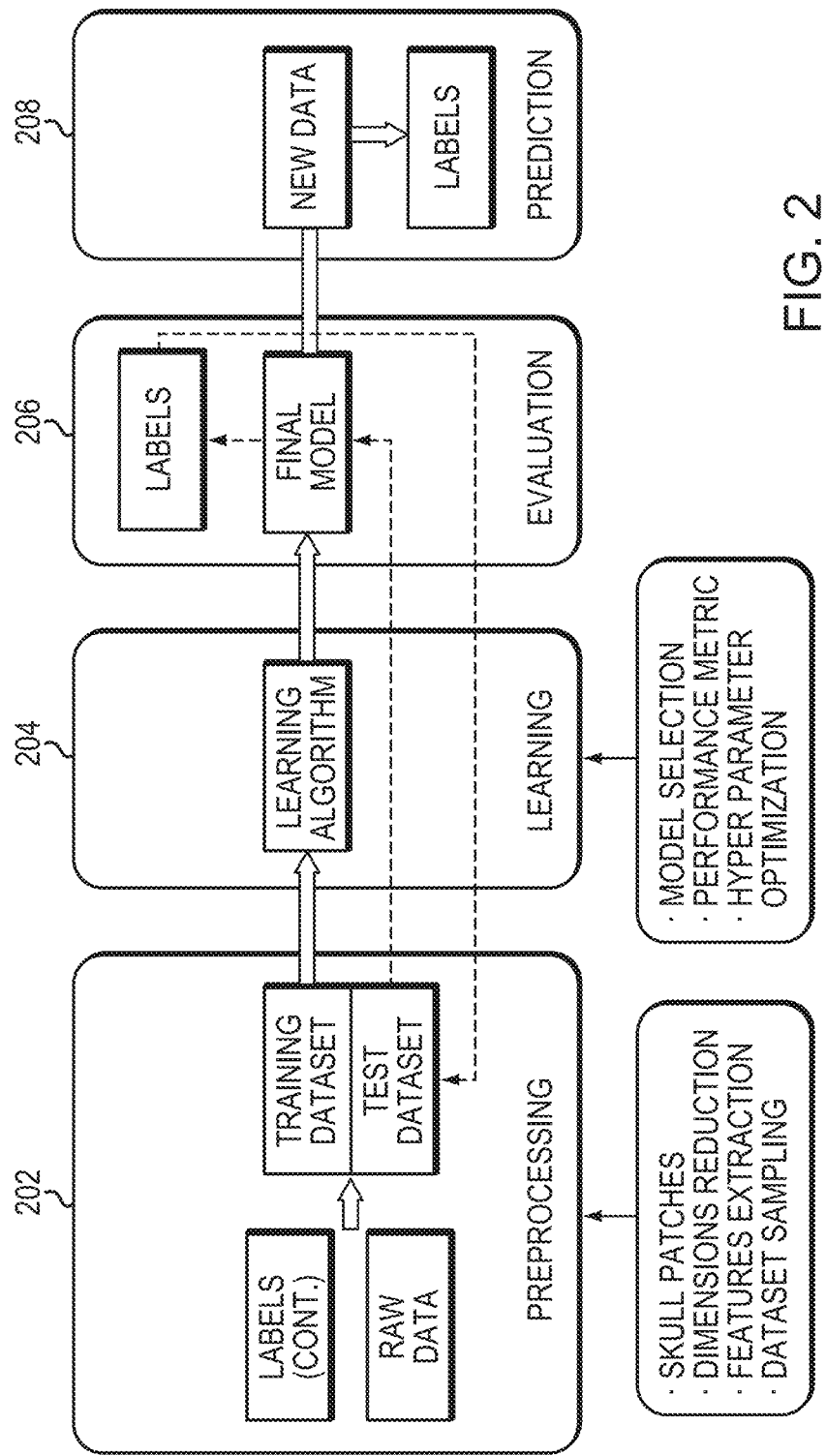
FIG. 2 illustrates an approach for estimating aberration effects on the ultrasound beam when traversing a patient's skull or other parts of the body in accordance with various embodiments.
Figure 3A:
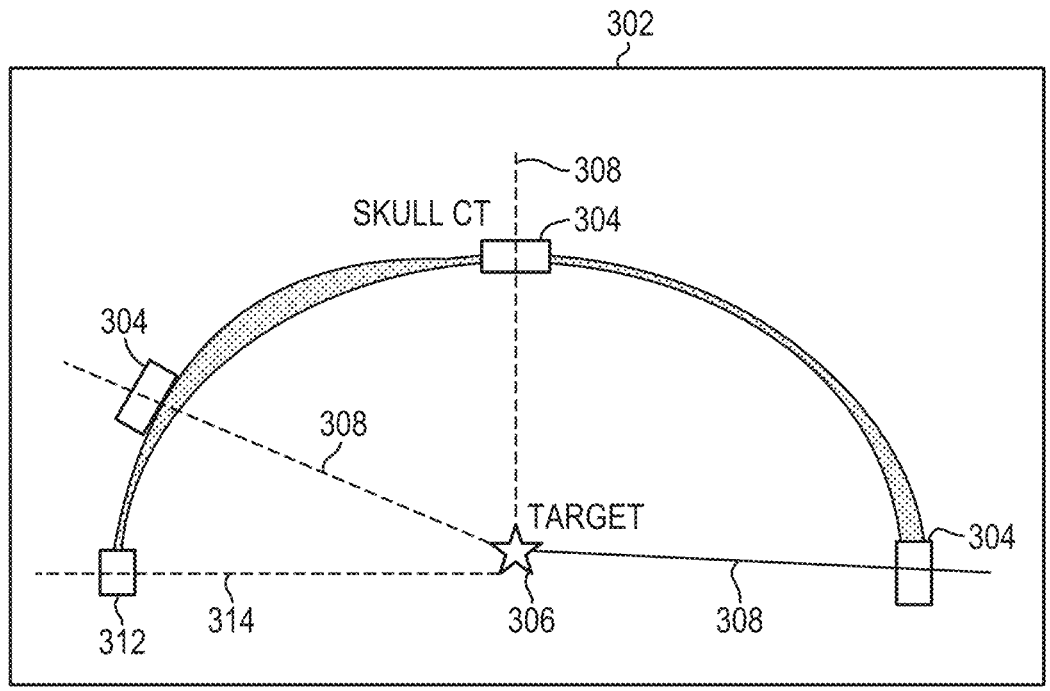
FIG. 3A, schematically depicts acquiring a series of images of the skull in accordance with various embodiments.

In various embodiments, prior to treatment, the aberration effects (such as phase shifts, time delays, etc.) on the ultrasound beam when traversing the skull 114 or other parts of the body are estimated using a precedent-based approach as depicted generically in FIG. 2. In a first step 202, a training set including various known skull features (such as the structure, shape, density, and/or thickness) and aberrations experienced by the ultrasound waves when traveling through the skull 114 is created. In one embodiment, the skull features are characterized based on images acquired using the imager 112. For example, referring to FIG. 3A, a series of images (e.g., computed tomography (CT) or MR images) of a human skull (or an animal bone) is first acquired in an ex-vivo system (e.g., a fluid-filled casing 302). Each image includes at least a portion of a skull patch 304 and may, in some embodiments, include more than one skull patch 304; the series of images may collectively cover the anticipated region of the skull through which the ultrasound waves travel (see FIG. 3B) prior to reaching a target region 306. Alternatively, a three-dimensional image of the skull may be reconstructed using the acquired series of images where the skull patches 304 are generated by the user based on the reconstructed image. In various embodiments, the images of the skull together with the locations of the transducer elements and the target region 306 are processed to determine traversing beam paths 308 between the transducer elements and the target region 306 and characterize the skull features associated with the skull patches 304 along the traversing beam paths 308. The characterized skull features may serve as a training data set and be stored in memory.

Figure 3B:
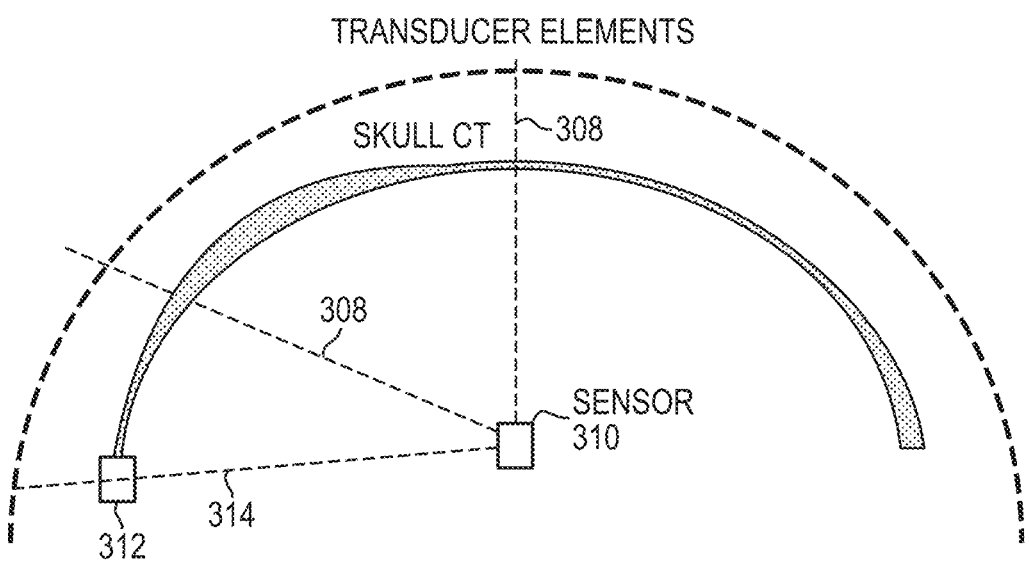
FIG. 3B, schematically depicts measuring aberrations of ultrasound waves caused by the skull in accordance with various embodiments.

Referring to FIG. 3B, in various embodiments, aberrations of the ultrasound waves caused by the skull 114 are measured using a sensor (e.g., a hydrophone) 310 placed at the target region 306. The sensor 310 may first detect the ultrasound pulses traversing fluid between the transducer 102 and the target region. After the skull is introduced in close proximity to the transducer (such that the transducer, target and skull are immersed in a water bath), the sensor 310 detects ultrasound pulses traversing each skull patch 304. Acoustic aberrations (which correspond to volumetric changes in the acoustic field, such as a phase shift and/or time delay) introduced as the pulses pass through the skull can then be determined based on the sensor measurements and stored as data of the training set. In one embodiment, the aberration measurement in the presence of the skull is performed multiple times at several target locations across the skull to increase the size of the training set. In addition, each measurement may be repeated one or more times to reduce noise.

Referring again to FIG. 2, in a second step 204, once a training set is created, a machine learning approach can be used to analyze data therein and, based on the analysis, to generate an inference function that maps the measured aberrations to the skull features. The machine learning approach may be data regression, data clustering or data classification as further described below, or any suitable approach known to one of skill in the art. Still in a step 204, other techniques, such as hyper-parameter optimization or model selection, are utilized in a conventional manner to tune various parameters of the learning process and create an updated inference function to optimize the performance on the training set (or at least a selected subset of the training set). In one embodiment, the updated inference function is evaluated based on data from a test set different from the training set (step 206). For example, referring to FIGS. 3A and 3B, the test set may include skull features of the patch 312 that are located on other traversing beam paths 314 different from the traversing paths 308 included in the training set (and obtained, for example, using a differently configured or differently positioned transducer array). Based on the skull features in the test set, the updated inference function may estimate an aberration associated with the patch 312. The estimated value is then compared with the aberration measured using the sensor 310. If the deviation therebetween and/or a statistical measure of the deviation is below a predetermined threshold (e.g., a mean phase error of 10° or other threshold corresponding to a clinically insignificant difference), the performance of the updated inference function is considered satisfactory and the updated inference function is stored in the system memory for later retrieval to predict aberrations in ultrasound waves traversing various skull features (step 208). If, however, the deviation between the estimated and measured aberrations is above the predetermined threshold, parameters associated with the machine learning approach are further adjusted; the evaluation process is repeated until the deviation between the estimated and measured aberrations is below the threshold or satisfies another suitable criterion.

Figure 4A:
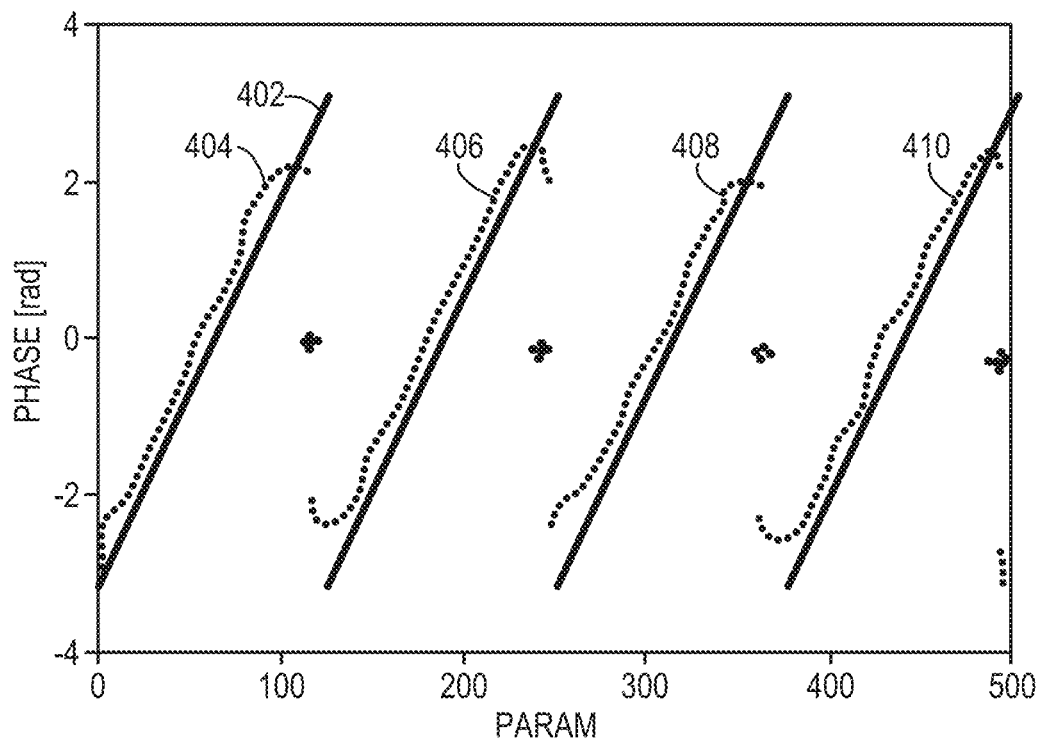
FIGS. 4A and 4B illustrate predicted relationships between ultrasound aberrations and skull features in accordance with various embodiments.
Figure 4B:
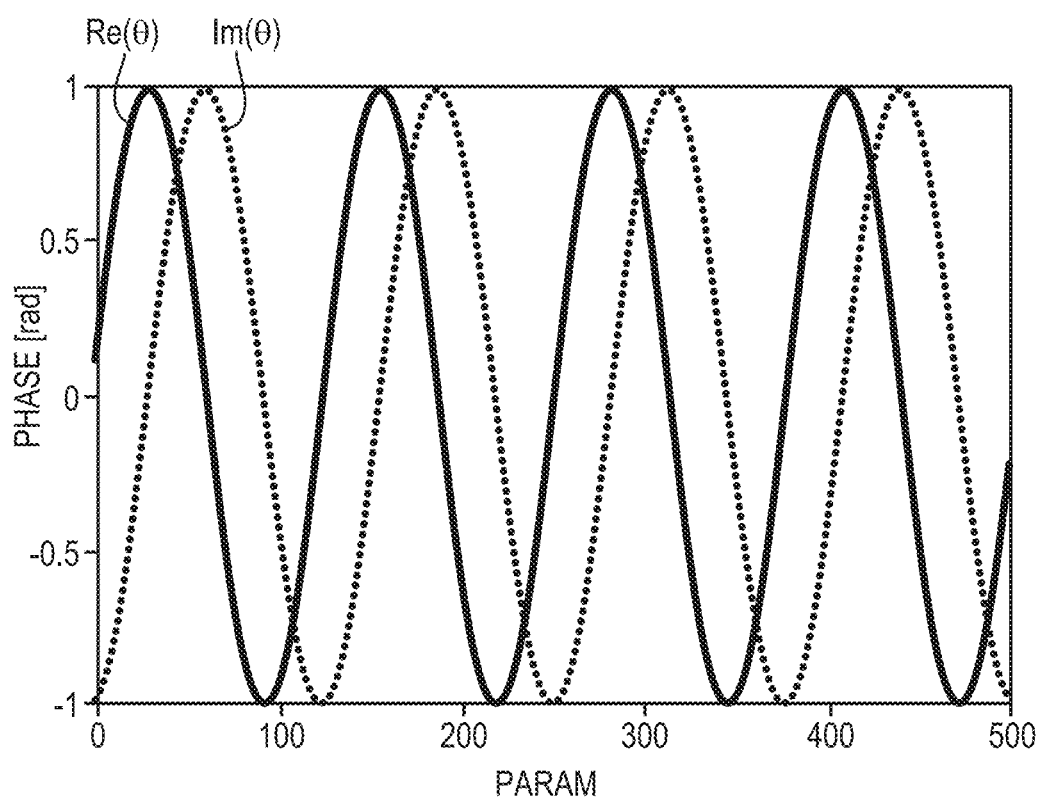

The measured aberration may be a phase shift, $\theta$, of ultrasound waves when traversing the skull. In some embodiments, the phase shift is defined in radians. Referring to FIG. 4A, in some embodiments, the phase shifts (in radians) and the skull features (e.g. its thickness) are predicted (e.g., using a physical model) to have a known (e.g., linear) relationship 402 using at least a subset of the data, defined by one or more ranges of the skull features. A regression is performed on the measured phase shifts against all the skull features to generate a relationship 404 between the phase shifts and the skull features (e.g., thickness). The generated relationship 404 generally matches the prediction 402, except that discontinuities occur at certain skull thicknesses. In one embodiment, the relationship 404 is stored in memory and retrieved at a later time to predict the phase shift of an ultrasound wave travelling through the skull. Alternatively, referring to FIG. 4B, the phase shift may be defined in complex form, $\theta = e^{-i\varphi}$, and thus having a real component, $\text{Re}(\theta)$, and an imaginary component, $\text{Im}(\theta)$. In one embodiment, the machine learning approach separately performs regressions on the real (cosine) and imaginary (sine) components to generate two inference functions that map the real component and imaginary component, respectively, to the skull features (e.g., thickness of the skull). Based on the two inference functions, a relationship, $f(\theta)$, between the phase shift, $\theta$, combining the real and imaginary components and the skull features can be obtained. The relationship, $f(\theta)$, may then be used to predict the phase shift of ultrasound waves traveling an arbitrarily selected skull region as long as the relevant features thereof are known (e.g., measured by one or more imaging modalities). The beamformer 106 in the ultrasound system can then adjust one or more of the parameters (e.g., phases $a_1$-$a_n$) associated with the n transducer elements to account for the inferred phase shifts induced by the skull, thereby improving focusing properties at the target region. The regression approach implemented herein may be a linear regression, a locally weighted regression or a nonlinear regression.

This machine-learning approach may be used for data classification (e.g., by defining classes each corresponding to a range of phase shifts, which may or may not be unwrapped as described below). In some embodiments, the detector device 122 measures beams reflected off the skull (e.g., from each skull patch 304 and/or from a small reflector at the target). The measured reflections may be added to serve as one of the skull features (e.g., by adding the real and imaginary components instead of the phases) using the machine-learning approach (e.g., data regression, data clustering, and/or data classification). In some embodiments, another suitable approach may be applied to add the measured phase shifts to serve as one of the skull features (e.g., as real and imaginary components) and use them for machine learning based on a conventional clustering technique (e.g., k-means clustering). In addition, the type of learning approach, for regression and/or classification, may include decision tree learning, association rule learning, similarity learning, supervised learning, unsupervised learning, online learning, artificial neural networks (shallow, deep, recurrent, or any other kind), etc., as understood by those skilled in the art and implemented without undue experimentation.

To avoid discontinuities and cyclicality as shown in FIG. 4A, in various embodiments, the predicted and measured phase shifts 402, 404—which are in the range of [0, 2×$\pi$]— are unwrapped. For example, the phase shifts in measurements 406, 408, 410 may be unwrapped by adding a constant, 2$\pi$×k, where k is an integer (e.g., 1, 2 and 3 for measurements 406, 408, 410, respectively), in each measurement; the resulting phase shifts $\varphi_{unwrapped} = \varphi_{measured} + 2\pi \cdot k$ are the unwrapped phase shifts closest to the physical model prediction 402. In another embodiment, based on the predictions 402, a linear fit of the phase shifts with respect to the skull features (e.g. thickness) may be obtained; and based thereon, an optimal k for which the resulting phase shift is the closest to the fit may be determined. Again, the measured phase shifts in measurements 406, 408, 410 may be unwrapped using $\varphi_{unwrapped} = \varphi_{measured} + 2\pi \cdot k$, where k is the determined optimal value for each measurement. In some embodiments, the measured phase shifts (which may or may not be unwrapped) may be analyzed and corrected before being used as a training set. In some embodiments, when a system shift is found in the measurement, the measured values may be corrected by removing the shift. This shift may be found, for example, by a phasor diagram of the measured ultrasound waves transmitted from the transducer elements that provide low acoustic amplitudes in fluid measurements only.

In various embodiments, the training set includes aberrations and/or reflections measured at various ultrasound frequencies. In one embodiment, the measured phase shifts are unwrapped as described above and subsequently rescaled based on the frequency at which they are measured. For example, the unwrapped phase shifts may be divided by the frequency, or multiplied by a factor, $$f_{fixed} / f_{measurement},$$

where $f_{fixed}$ and $f_{measurement}$ represent a predefined fixed frequency and the frequency at which the phase shifts are measured, respectively.

In various embodiments, the acoustic intensity at the target associated with each skull patch 304 and/or transducer element 104 is predicted based on the features associated with the skull, as well as the element 104 and the measurement setup using the physical model. Additionally or alternatively, the sensor 310 may measure the intensity at the target; the measured intensities may then be analyzed using the machine-learning approach, such as regression or classification (e.g., setting classes to each cover a range of intensities) as described above to predict acoustic intensities resulting from various skull features. The predicted intensities may be used, for example, to adjust the beamformer 106 in the ultrasound system 100 to account for the skull absorptions, thereby reducing the skull heating and improving treatment safety.

In one implementation, a binary classification model is applied to predict whether the intensity of the beam transmitted by an element is sufficient (e.g., above a predefined threshold to achieve a desired clinical effect and/or eliminate undesired effects) after traversing the corresponding skull region. Only elements 104 whose emissions are predicted to have sufficient intensity at the target are activated during treatment. A learning model (e.g., another binary classification) may be used to estimate the reliability of the predictions obtained using the original model and thereby activate only elements whose phase shift prediction is sufficiently reliable.

In some embodiments, the machine learning approach utilizes a model that maps the measured aberrations to the skull features. The model may be a decision tree, a random forest, a CART model, a multilayer perceptron (e.g., a neural-network classifier), a k-nearest neighbors algorithm, or other learning approach known to one of skill in the art. The model may implement a regression or a classification, depending on the task; for example, the model may output a continuous value that represents the phase shift (regression) or select among available classes, each representing a range of possible phase shift results, e.g., 10 classes each covering a range of 36 degrees (classification).

Figure 5A:
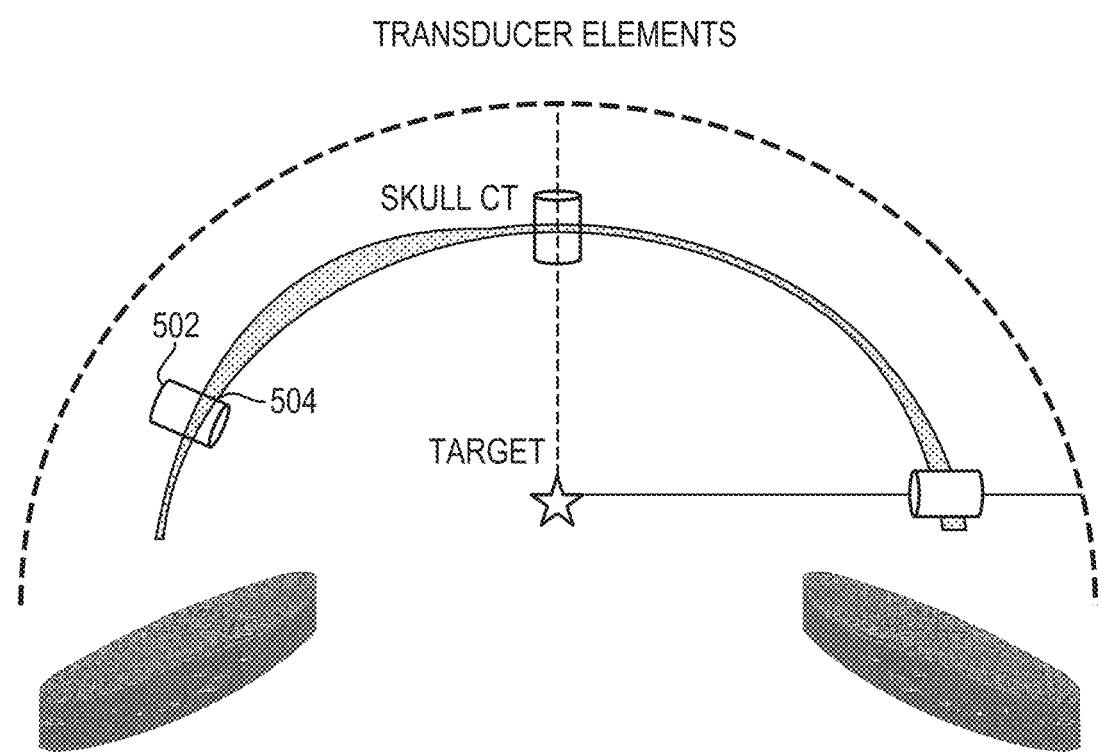
FIGS. 5A-5E depict an approach for extracting various skull features in accordance with various embodiments.
Figure 5B:
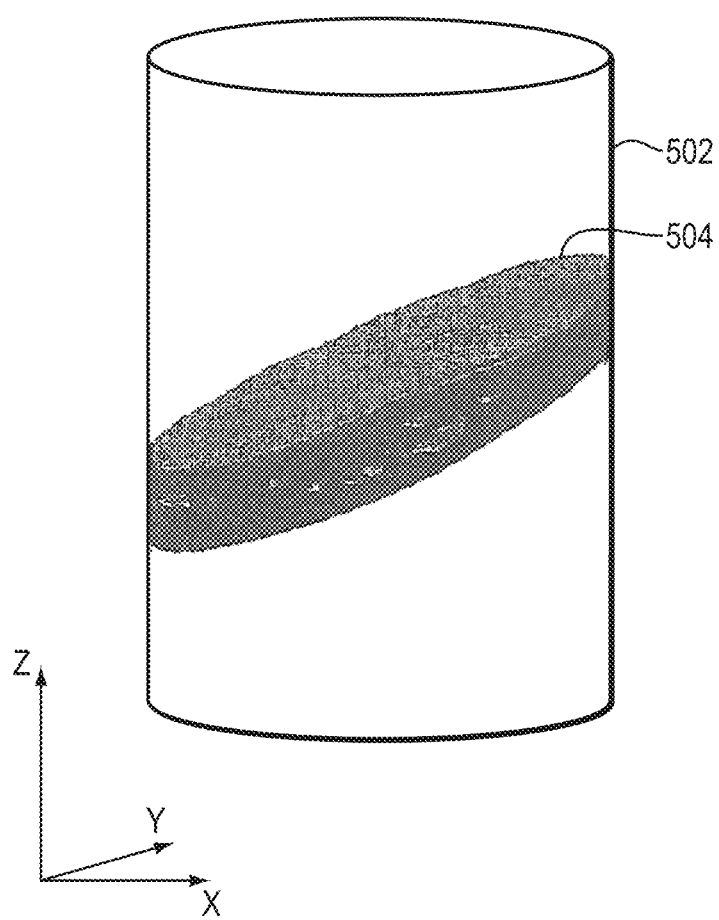

In one embodiment, a convolutional neural-network model including a suitable number (e.g., five) of convolutional layers and a suitable number (e.g., three) of fully connected layers is implemented to classify data in the training set. The input to the first convolutional layer may be m×m×r (e.g., 224×224×3) images, where m is the height and width in pixels of the image and r is the number of channels (for example, an RGB image has r=3). The input images may include or consist of images of the skull patches 304 acquired by the imager 112 as described above. Additionally or alternatively, the input images may include or consist of images generated (e.g., resampled and/or interpolated) from the images acquired by the imager 112 as further described below. FIGS. 5A and 5B depict an exemplary imaging volume 502 and skull volume 504 inside the imaging volume 502. In order to have a uniform representation for all transducer elements 104 in all measurements, an element-related Cartesian coordinate system may be used. For example, as depicted in FIG. 5B, the z coordinates may be in the direction of beam propagation, the x and y coordinates may be in the directions perpendicular to beam propagation, and the origin may be at the location of the transducer element 104. In one embodiment, the size of the imaging volumes 502 is fixed for all samples. In addition, the location of the imaging volume 502 along the z axis may or may not be fixed for all samples. In one implementation, the image volume 502 is taken with a smaller range of locations along the z axis around the skull center of mass to reduce input sparsity. In that case, information regarding the location of the imaging volume 502 along the z axis (i.e., the direction beam propagation) may be provided to the machine-learning model as well.

Figure 5C:
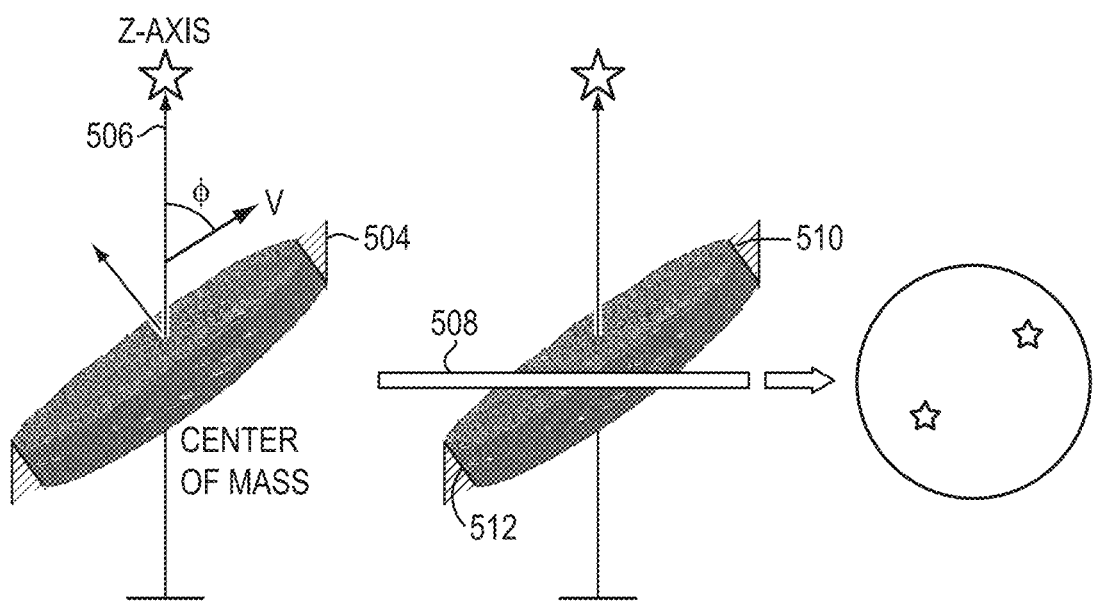

As depicted in FIGS. 5A-5C, while the orientations of some imaging volumes 502 are aligned with the directions of acoustic beams emitted from the transducer elements 104 to the target region 306, the skull volumes 504 may not be; thus, a tilting angle, Φ, between the orientation, $\vec{v}$, of each skull volume 504 and the acoustic beam 506 may exist. FIG. 5C depicts an approach for determining Φ. In a first step, the acoustic beam path 506 is determined based on the locations of the transducer element and the target; the beam path 506 is defined, in the illustrated embodiment, as the z-axis in the Cartesian coordinate system as described above. The transducer location may be obtained using, for example, a conventional time-of-flight method or any other suitable method, and the target location may be determined based on the images acquired using the imager 112. Coordinates of the skull, transducer elements, and/or target location can be registered using any suitable registration and/or transformation approach; an exemplary approach is described in U.S. Patent Publication No. 2017/0103533, the entire disclosure of which is hereby incorporated by reference. By applying the imaging registration, images acquired using one system can be transformed into and combined with images acquired using another system. Additionally or alternatively, coordinates of the skull may be registered in the transducer coordinates, using mechanical design of skull holder frames.

In a second step, the location of the center of mass (COM) of each skull volume 504 is determined by conventional image-analysis techniques, and subsequently, a center plane 508 passing through the COM and perpendicular to the beam path 506 can be defined. The center plane 508 divides the skull volume 504 into an upper region 510 and a lower region 512 and is defined in the figure as the x-y plane in the Cartesian coordinate system. In a third step, the locations of the COMs of the upper and lower regions 510, 512 are determined. In a fourth step, the vector $\vec{v}$ connecting the COMs of the upper and lower regions 510, 512 is computed as $\vec{v} = COM_{upper} - COM_{lower}$. Finally, the tilting angle Φ can be determined computationally based on the vector $\vec{v}$ and the z axis. The determined tilting angle Φ may be included in the training set to serve as one of the skull features. This procedure is repeated for all of the imaging volumes 502, or at least for those whose skull volumes may not be aligned with the acoustic beams passing therethrough. Other imaging data extracted from the images, e.g., skull segmentation followed by a linear fit, may be used alternatively to or cooperatively with the vector $\vec{v}$ to determine the tilting angle Φ.

Figure 5D:
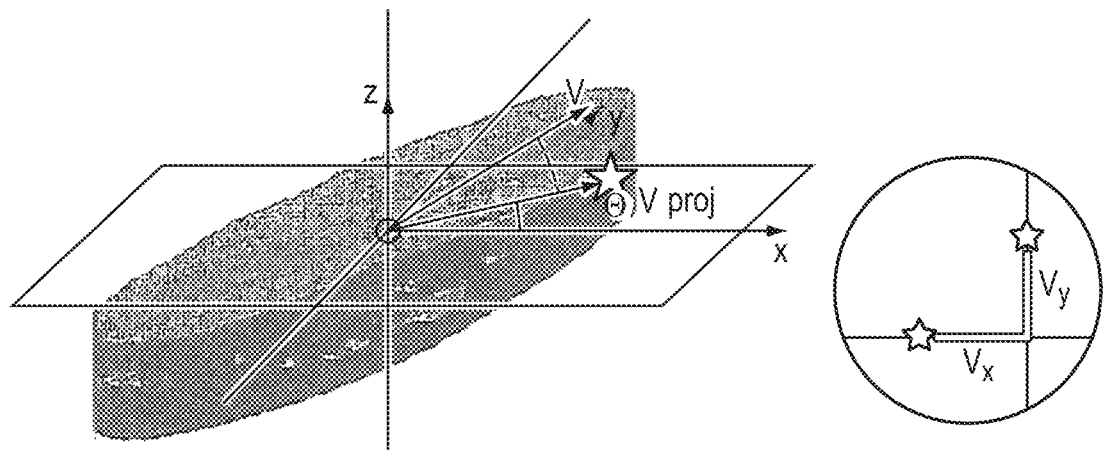
Figure 5E:
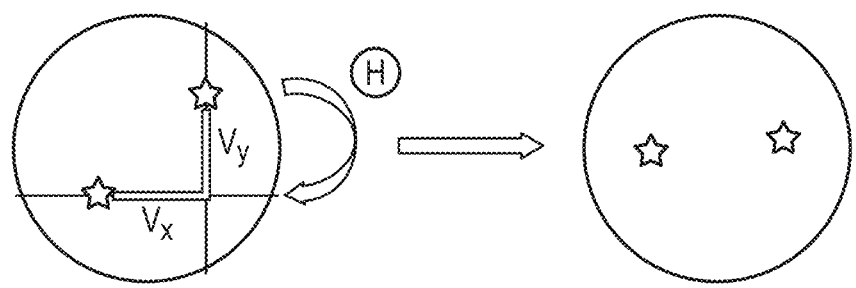

In various embodiments, prior to inputting the skull patches into the convolutional neural-network model, a rotation angle, Θ, of each skull patch around the z-axis with respect to the x-z plane is first determined. FIGS. 5D and 5E depict an approach for computationally determining the rotation angle Θ associated with each skull patch. In a first step, the vector $\vec{v}$ connecting the COMs of the upper and lower regions 510, 512 is projected onto the x-y plane to compute a projection vector, $\vec{v}_{proj}$: $\vec{v}_{proj}=(v_x, v_y, 0)$. In a second step, the rotation angle Θ is determined based on the x and y components of the projection vector $\vec{v}_{proj}$: $\Theta = \tan^{-1}(v_y/v_x)$. In some embodiments, a new patch volume having a rotation angle of the determined angle Θ with respect to each imaging volume 502 is resampled and/or interpolated from the image volumes 502 and/or from the images acquired by the imager 112. A collection of the new patch volumes is then included in the training set and used as input to the convolutional neural-network model. Alternatively, the skull patch 504 may be rotated with respect to the x-z plane based on the determined angle Θ, and after rotation, the vector $\vec{v}$ of the COMs lies on the x-z plane. The rotation process may be applied to some or all skull patches, and the determined rotation angles may also be included in the training set to serve as one of the skull features.

In addition to the imaging data described above, various characteristics (e.g., the angle of the acoustic beam 506 with respect to an outer plane of the skull, the angle of the beam 506 with respect to an inner plane of the skull, the skull density ratio (SDR), the average image intensity of the skull (in quantitative scale units, such as Haunsfield) or the average image intensity of each layer of the skull) may be extracted from the images of the skull, transducer elements and/or the target, and added to serve as skull features in the learning model. An exemplary approach for computing the SDR is provided, for example, in U.S. Patent Publication No. 2016/0184026, the contents of which are incorporated herein by reference. In addition, features that are not directly related to the skull (e.g., the ultrasound frequency, the location of a transducer element in spherical coordinates, the size, shape and/or orientation of a transducer element, the measurement case serial number, the phased array transducer serial number, a prediction of the phases and the amplitudes of the transducer elements based on a physical model, observed deviations of physical-model predictions from measurements, a comparison between a phase prediction error using the physical model and a predetermined threshold, formation of the shear waves, etc.) may also or alternatively serve as skull features. Further, features extracted from additional measurements, such as reflections, spectral activities, etc.) may also be included in the skull features.

In various embodiments, before providing the images to the learning model, standard machine-learning preprocessing may be performed on the images. For example, the images may be normalized by subtracting the mean therefrom and dividing by the standard deviation. These preprocessing techniques may also be performed on any or all skull features (e.g., thickness).

Figures 6A, 6B, 6C:
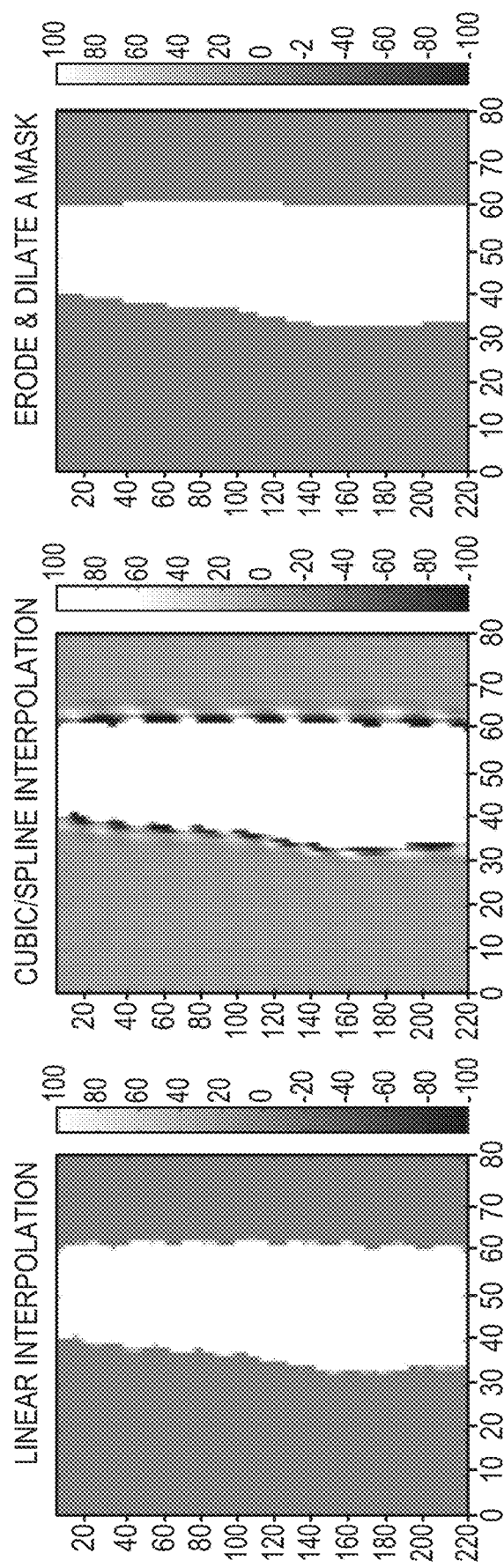
FIGS. 6A-6C depict various approaches for smoothing boundaries of a skull image in accordance with various embodiments.
Figure 7A:
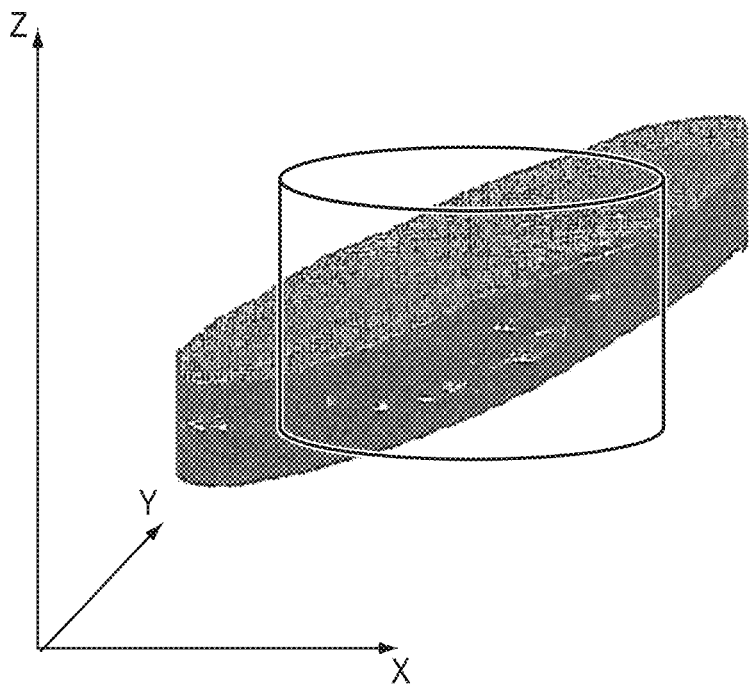
FIGS. 7A-7D illustrate various approaches for slicing skull images in accordance with various embodiments.
Figure 7B:
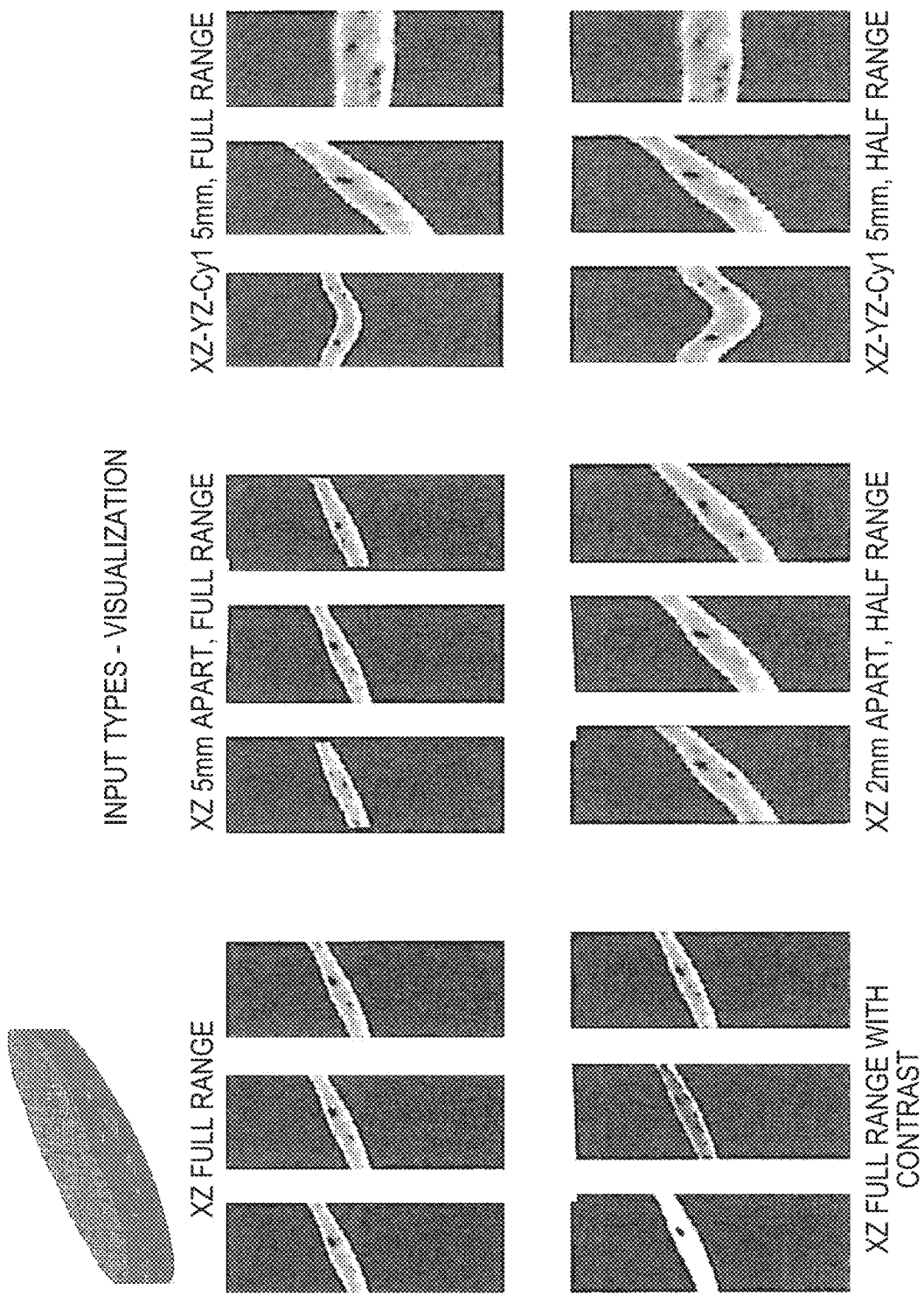
Figure 7C:
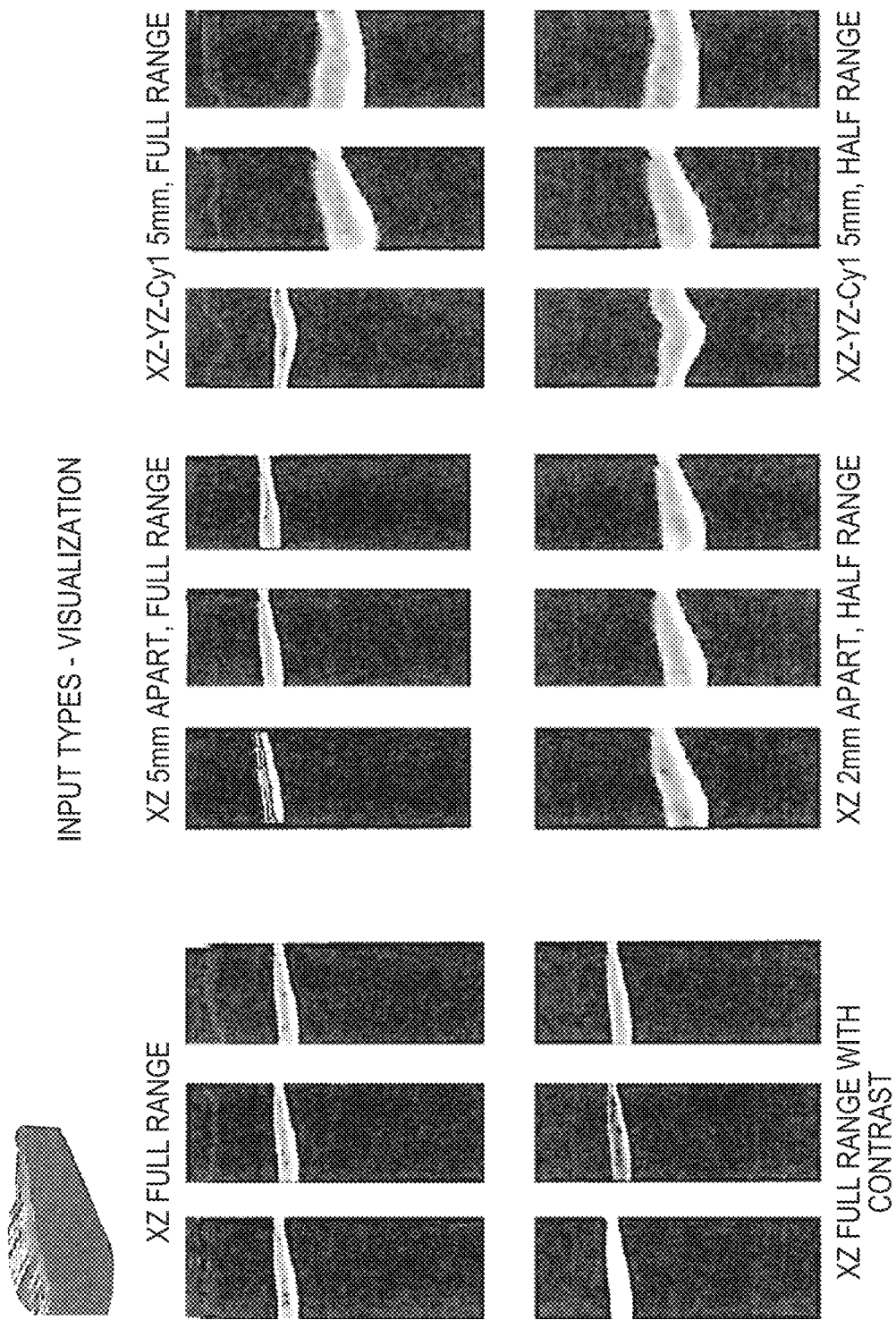
Figure 7D:
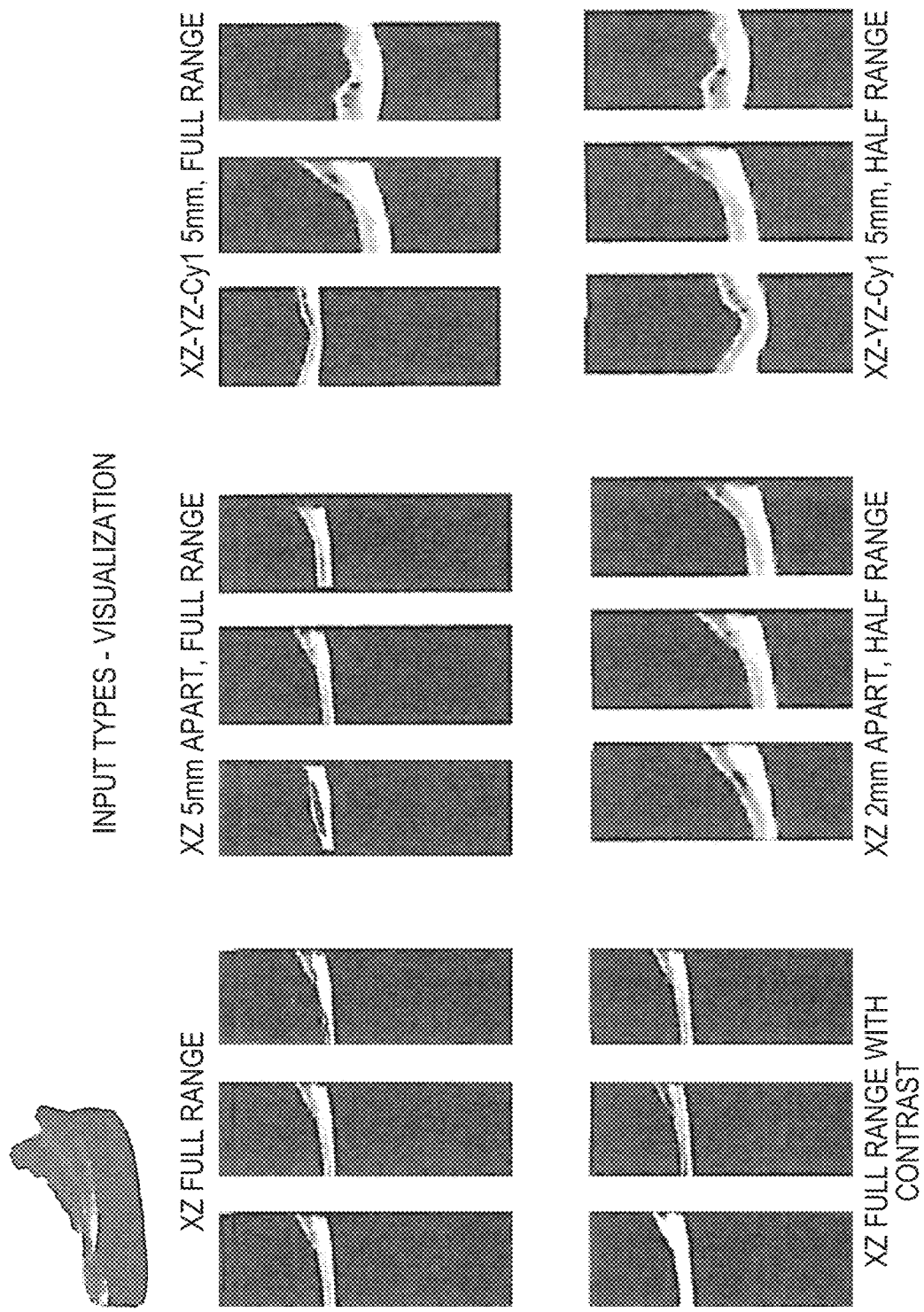

In some embodiments, the images acquired using the imager 112 have different resolutions for different orientations. This may cause the skull volumes 504 to have different boundary shapes. Various approaches may be implemented to process the images so as to accurately acquire the skull features based on a consistent boundary. For example, augmented data based on additional images where the resolutions are different may be used cooperatively with the images originally acquired. In addition, various known approaches may be applied to smooth the boundaries of the skull volumes. In some embodiments, augmentation data is extracted from the same, originally acquired images but with a reduced resolution (e.g., by ignoring at least a portion of the data). Additionally or alternatively, skull boundaries may be smoothed by creating images (from the CT images) having a uniform resolution using, for example, linear interpolation, and/or cubic/spline interpolation as depicted in FIGS. 6A, 6B, respectively. In addition, an erosion and dilation mask depicted in FIG. 6C may be used to further smooth the boundaries.

Because the orientation vectors of the skull patches after rotation all lie on the x-z plane, image consistency of the input images taken from slices (e.g., on the x-z plane) of the skull patches may be ensured. This is because the skull patches are rotated around the z-axis (which is the acoustic beam path 506) without changing the tilting angle, Φ, with respect to the beam path 506 or the distances between the patches and the beam path 506;—patch rotations do not change skull features associated with the beam path 506. In some embodiments, the asymmetry of the element shape in the x-y plane is insignificant. For example, the orientation of a circular element or a square element may be randomly arranged on the phased-array transducer; the skull regions through which the ultrasound waves travel remains unchanged after the patch rotation.

In another embodiment, instead of aligning all skull patches prior to providing them to the learning model, the learning model may be given rotated duplications of the original measurements in order to extend the training set. (Again, as with all input data provided to a learning model, the model uses this data to predict, based on its inference algorithm as previously trained, a parameter relevant to beam energy at the focus.) For example, triplets of the images slices separated by an angle of 120° with respect to the z-axis may be obtained and provided to the learning model. In some embodiments, the input images are sampled in multiple orientations having an angle difference of 30° between two consecutive images in order to augment the data; this creates a larger training set without the need to obtain additional images.

In still another embodiment, the training set is created based on processed images, i.e., images that have undergone some degree of analysis or refinement (except resampling or interpolation). For example, image slices of the skull processed so as to reveal or emphasize skull density may be used. Generally, the human skull includes three layers (i.e., an external cortex layer, a marrow layer, and an internal cortex layer), each having different and varying densities; hence, the ultrasound-affecting properties of a skull image can be predicted with greater precision by estimating the proportion of each layer in an image and using, for predictive purposes, a weighted-average density based on the estimated proportions and image intensities. In one embodiment, the spatial size and resolution of the image slice are defined (e.g., a slice having a region of 14×14 mm in the x-y plane may be represented by 8×8 pixels); each pixel is associated with a ray at the matching x and y coordinates and with z from the element 104 to target. Each ray is represented by points along it with a predefined spacing, and each point along a ray is provided with a value taken from the original images or its derivatives (e.g. the CT image intensity in Haunsfield unit, or the image intensity after using a smoothing filter or the image gradient value) at the relevant location. From those values, various parameters known to be significant for acoustic aberrations can be extracted, e.g., the skull thickness experienced by a particular observed ray, the skull density variance along that ray, etc. Also, some parameters can be extracted by combining data of several rays, e.g., by using every 4×4 rays to create a skull outer surface plane fit, which may be employed to obtain the outer angle per groups of rays (facilitating use of a matrix of lower dimensions then that characterizing the original points).

The CT intensities along the parallel rays from the transducer element 104 to the focus at the target region are first determined; for each ray, the range of each skull layer can be determined and then each ray may be assigned a per-layer characteristic, such as a minimum, a maximum, an average or a standard deviation of the CT intensities (in quantitative scale units). The image slices are created based on the CT intensities of each ray encountering the skull. These image slices may also be combined with other slices (e.g., images in the x-z and/or y-z plane). In some embodiments, these image slices are further processed to generate an image gradient. In one implementation, the images are created such that their pixel intensities correspond to a parameter (e.g., the thickness, skull angle and SDR) that can be computed on a per-pixel basis inside the skull. These images may then be combined, e.g., as channels of the input or given in parallel to different layers and/or neural networks.

In various embodiments, 2D (e.g., 224×224 pixels) convolutional layers (e.g., 3 layers), with or without pooling, for each image are separately obtained; the skull features associated with each layer are concatenated and passed onto a fully connected layer. This can be performed for different images using pixel values (e.g., 8×8 pixel thickness slices, 224×224 pixel xz slices, 112×112 pixel yz slices or 16×16 pixel thickness slices) and values of other feature parameters (e.g., a 16×16 array of values for the incident angles of imaging rays entering the outer surface of the skull, an 8×8 array of mean intensity values for each imaging ray, and an 8×8 array of standard deviations of the marrow intensity along each imaging ray). This technique can also be applied to images acquired using different imagers.

An ensemble of neural networks based on the fully connected layer and/or other learning models can then be established. For example, a neural network may include multiple neurons each representing a different learning model; the trained weights of the first (and possibly the only hidden) layer may be used as weights for each model for combining the final results thereof. In some embodiments, a pixel-wise mapping is established between images (e.g., being 5 mm apart, the same location in different images may exhibit different averaging/contrast), and corresponding regions of multiple images may be provided as channels to the same convolutional layer.

Referring to FIGS. 7A-7D, various approaches may be used to slice the rotated skull patch images depicted in FIG. 5E and/or other types of images as described above for purposes of creating a training set for the convolutional-neural-network model. For example, one approach takes slices in the x-z plane each of which passes through the COM of a skull patch, and uses these images as input to the first convolutional layer. Using this approach, the image inputs may include a full image of each skull patch in the z direction (e.g., in the direction of beam propagation from the transducer element to the target). In another approach, three slices in the x-z plane with a distance of 5 mm therebetween are acquired and used as image inputs. In still another approach, three slices on the x-z plane with a distance of, e.g., 2 mm therebetween and including a partial image in the z direction are used as an input. The skull COM may be located at a middle position in the partial image. In one embodiment, the same slice on the x-z plane having different contrasts and/or thresholds of cutting the minimal and maximal pixels intensities may be provided. In some embodiments, the input images include one image slice on the x-z plane, one image slice on the y-z plane, and one image taken by intersecting, with the skull patch, a cylinder having a radius of, e.g., 5 mm and oriented parallel to the z-axis; again, each of the images may include a full image or a partial image in the z-axis direction.

The above-described approaches to selecting input images of the skull for purposes of training and testing, and ultimately operation of the machine-learning model, are for illustration only; the present invention is not limited to such approaches. One of ordinary skill in the art will understand that variations are possible and are thus within the scope of the present invention. For example, the skull patches in the training data set may be rotated with various orientations to extend the training data set. In one embodiment, a series of images rotating along the z direction are acquired; the middle slice may include the skull COM and the other slices are located with respect to the middle slice. The data may be augmented with images that are rotated around the z axis and providing the same labeling or by images that are added with some noise. In addition, the training data set may be augmented with several aspects of the same redundant data. Extension and/or augmentation of the training set as described above may improve performance and reduce the chances of overfitting the aberration-prediction model (with the tradeoff of increasing the processing resources and/or time).

Upon receiving the input images, the learning model may extract meaningful features associated with the input images in accordance with its intrinsic mode of operation. In some embodiments, the learning model uses input features extracted by a neural network that was trained with the input images. For example, the weights may be extracted from a fully connected layer in a convolutional neural network that is pre-trained on a large set of images. The neural network may be proprietary, self-constructive and/or adapted from other tasks (i.e., transferred learning) for expediting and increasing performance of the learning process. In another approach, autoencoders are utilized to directly extract features from the input images.

The learning model may also implement manual features engineering, e.g., combining prior knowledge of the problem with image-processing techniques and other factors known to affect the end result. The features may be, for example, the tilting angles Φ between the skull patches and the acoustic beam path 506, the skull width of the patches, the skull patch skewness, the skull density variance and/or other skull features. Feature extraction may also be performed using any suitable algorithm, such as principal component analysis (PCA), scale-invariant feature transform (SIFT), etc. In addition, the features may be extracted after the images are processed to generate an image gradient and/or filters for processing subsequently obtained images.

In one embodiment, beam properties (e.g., a phase shift or an intensity) at the target region after travelling through the skull are predicted using a physical model. A neural network (or any other learning model) can be trained using the results predicted by this model. This approach provides the neural network with a much larger training set than that obtainable using actual measurements. The model results may be augmented with noise (which may be skull-patch dependent) before being used as labels in the learning process in order to simulate real measurements obtained in clinical practice.

In some embodiments, after training by using the prediction results, the learning model is adapted to the actual measurements, e.g., by fine-tuning.

In addition, the training set may include multiple sets of skull-related features (e.g., thickness, angles) extracted from the skull patches or directly from the imager 112, each set corresponding to a different processing parameter (e.g., having a different sensitivity to the CT intensities in Haunsfield units). Each set of extracted features can provide the basis for training a learning model; an ensemble neural network including one or more of the learning models can then be created. In one implementation, the skull features extracted from images obtained using different imaging sensitivities can be used to create a 2D matrix (e.g., one dimension corresponding to a CT sensitivity and the other dimension corresponding to the skull features); the 2D matrix can then be used to train a learning model (e.g., a neural network having a convolutional layer on the sensitivity dimension (no pooling) followed by a two-dimensional convolutional layer).

In various embodiments, an input to the learning model includes three separate xz slices and three images that correspond to different beam intensities after travelling through the skull and, if desired, having manually engineered features. The xz slices may be passed through one or more convolutional layers; in parallel, the intensity images may also be passed through a separate set of one or more convolutional layers. The resulting features of the parallel paths may be concatenated with each other and with the manually engineered features, if present. Finally, the concatenated features may be passed through one or more fully connected layers for classification or regression.

In another embodiment, recurrent neural networks are implemented in order to associate patches in the same measurement and/or the same patient's skull, as well as measurements from the skull patches corresponding to the same skull area. In this case, the training set is ordered by measurement cases and skulls, and optionally by skull patch positions within each measurement case. In addition, the training set may include unlabeled data for unsupervised learning. In one embodiment, the unlabeled data is used in a clustering approach to obtain insights into factors that can serve to classify features. In another embodiment, the unlabeled data is used in supervised learning for regularization purposes. As used herein, a measurement case denotes a single measurement of ultrasound aberrations resulting from travel of acoustic beams through one or more skull patches.

Figure 8A:
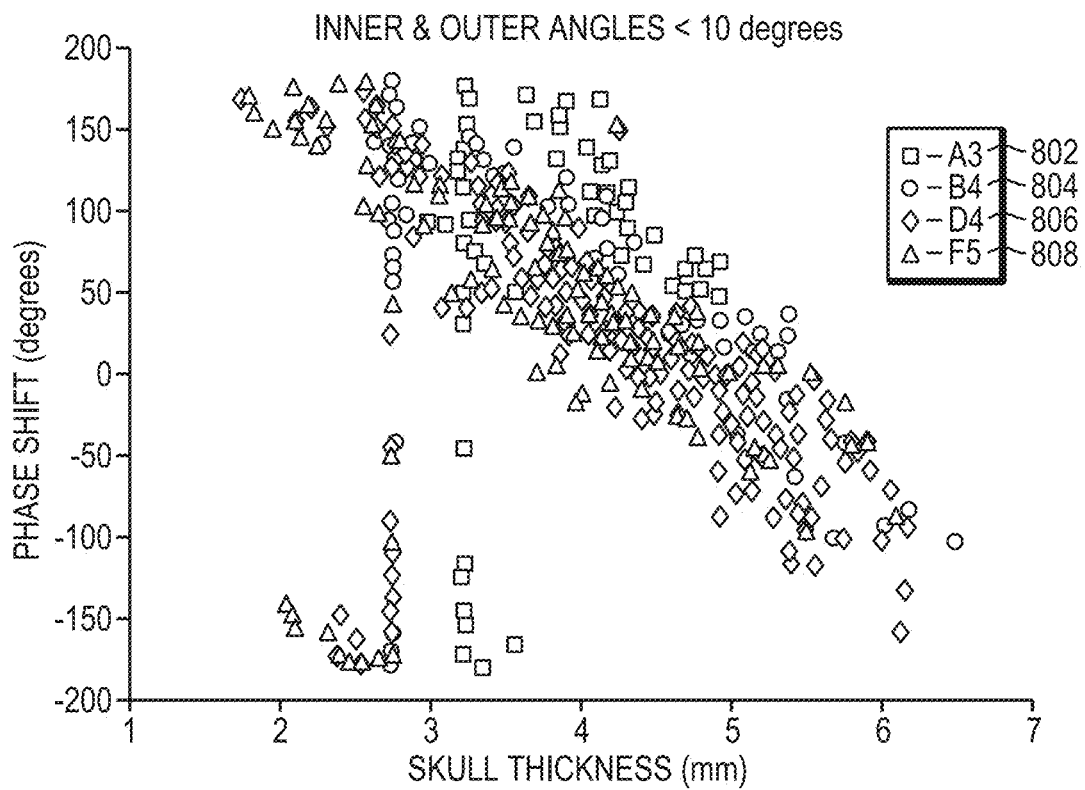
FIGS. 8A-8F illustrate relationships between an acoustic aberration and a skull feature in accordance with various embodiments.
Figure 8B:
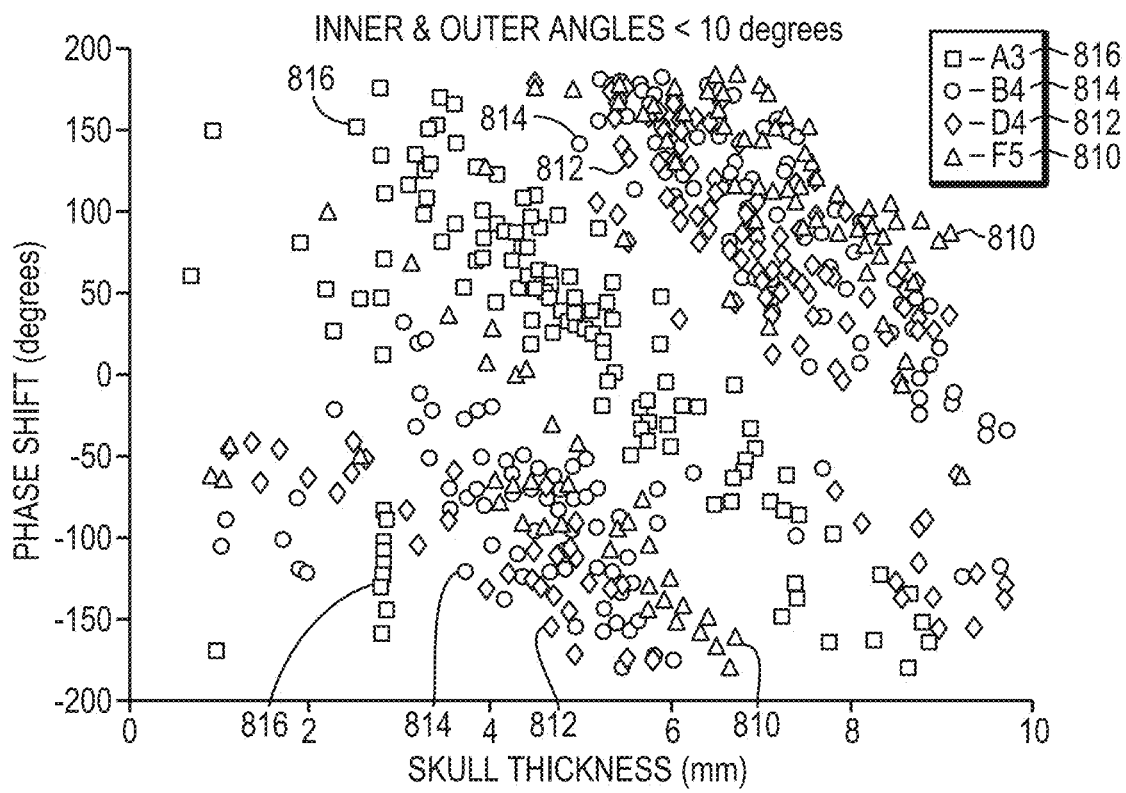

In various embodiments, the acoustic aberrations are phase shifts. FIG. 8A depicts a relationship between the measured phase shifts and the skull thickness in four different measurements 802-808 of a skull (each measurement having a unique setup, i.e., taken from images obtained separately using different imaging parameters). The phase shifts generally negatively correlate to the skull thickness and data from the four skull measurements 802-808 collapses, i.e., becomes undifferentiated. FIG. 8B depicts another relationship between the phase shifts and the skull thickness in four different measurements. Although the phase shifts remain negatively correlated to the skull thickness, data from the four measurements no longer collapses. This may be caused by a change in the temperatures of the media (e.g., the liquid between the transducer and the target region and/or different skull properties). Accordingly, it is important to ensure that when measuring aberrations in the presence of the skull, the temperature of the skull and filled liquid is the same as that of the filled liquid when measuring acoustic waves in the absence of the skull. Alternatively, measurements of all skulls can be measured at a substantially similar temperature corresponding to that of the filled liquid.

Figure 8C:
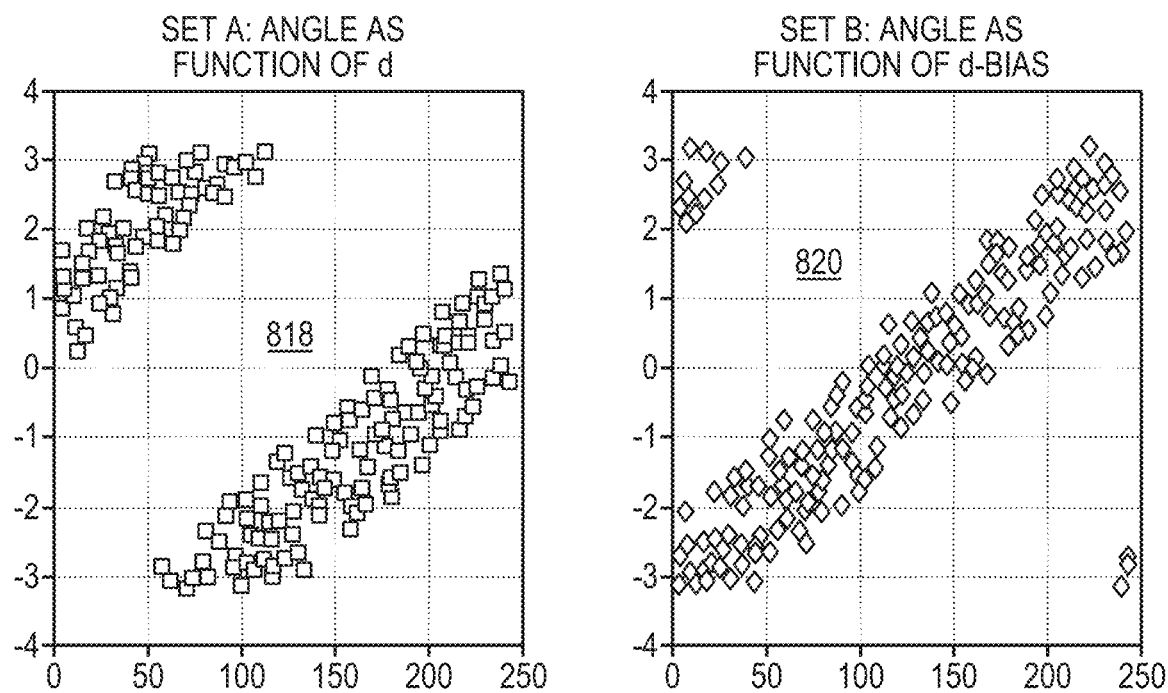

Alternatively, the difference between the phase shifts in different measurements (e.g., 802-808) may be quantified as further described below; data from the four measurements 802-808 may then be corrected based on the quantified difference and thereby collapses. In one embodiment, changes in the environmental conditions (e.g., the temperature of the media) are assumed to be insignificant during the measurement of each one of the skull measurements 802-808 (e.g., one minute per measurement using 1000 transducer elements); thus, a phase bias caused by the temperature change during each measurement can be considered as constant. With reference to FIG. 8B, data sets 810-816 may have constant biases $PB_1$-$PB_4$, respectively. The difference between the phase biases $PB_1$-$PB_4$ of different skull measurements can then be computed based on a constant distance between the linear relationships correlating the phase shifts to the skull thickness. For example, referring to FIG. 8C, two different measurements (i.e., data sets A and B) 818, 820 may have different phase biases relative to a predefined reference. The difference, D, between the two phase biases 822, 824 at each skull thickness may be computed as $$D_j = \text{angle}[e^{i \times \varphi_j^A}(e^{i \times \varphi_j^B})^*],$$

where j indexes different skull thicknesses in a data set, $D_j$ is a phase bias difference, $\varphi_i^A$, $\varphi_i^B$ are the mean phases of the transducer elements associated with a thickness j in a defined range from data sets A and B, respectively, and * denotes a complex conjugate. Alternatively, the phase may be computed as $$\varphi_i^X = \text{angle}\left(\sum_{m=1}^{N_i} e^{i \times \varphi_m}\right),$$

where $N_i$ is the number of elements in a data set X corresponding to a thickness i in a defined range, and $\varphi_m$ is the phase shift measured for an element m. The summation may be weighted by the amplitude of the measurements per element.

Figure 8D:
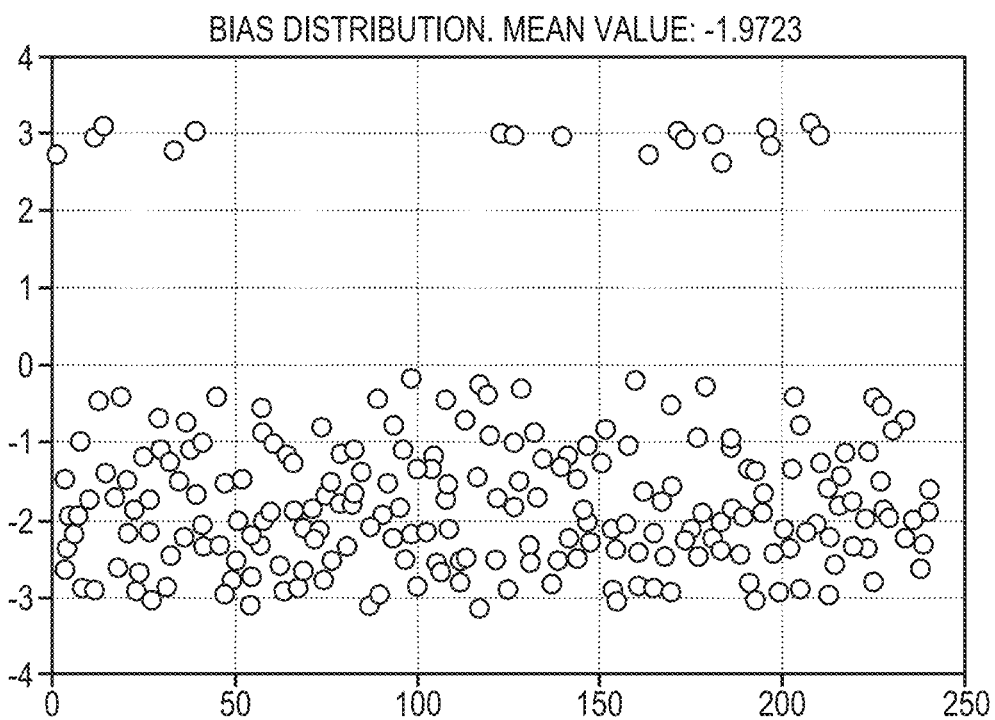

FIG. 8D depicts a distribution of the phase-bias difference, D, over the skull thickness. As shown, the difference between the phase biases of data set A and data set B is roughly 2 radians. In one implementation, the average of the difference over the entire range of skull thickness is computed; the average difference is then used to correct the data set B such that it overlaps with data set A. In another implementation (that better handles wrapping affects), the median of the phase-bias difference D over the entire range of thicknesses is first computed and applied to correct data set B. A phase-bias difference D' between the data set A and the corrected data set B' can then be determined. Subsequently, the average phase-bias difference over the entire range of thicknesses is computed and applied onto data set B' to generate a data set B" that overlaps with the data set A. In another embodiment, the phase-bias difference D' between A and B' is determined by performing a linear fit for each data set and subsequently computing the distance between the fits.

The phase differences between measurements may also result from other factors, such as skull inhomogeneity. These may cause different slopes and offsets in the linear relationship correlating measured phase shifts to skull thickness (e.g., data sets 826, 828 in FIG. 8E). These factors may be discarded in a bias calculation using a model (e.g., a physical model), allowing the model to learn the skull-related contribution to the bias and correcting only the bias resulting from the measurement setup. The physical model may estimate the phase shifts of the ultrasound beams when traversing various parts of the skull based on, for example, CT images of the skull and/or prior measurements of the transmitted and/or reflected waves from the skull. The physical model provides unbiased estimations of the phase shifts through various skull regions and need not accurately predict the aberrations. Alternatively, the machine learning model as described above can be used during its training process to correct the bias of additional training data based on the trained model established so far.

Figure 8E:
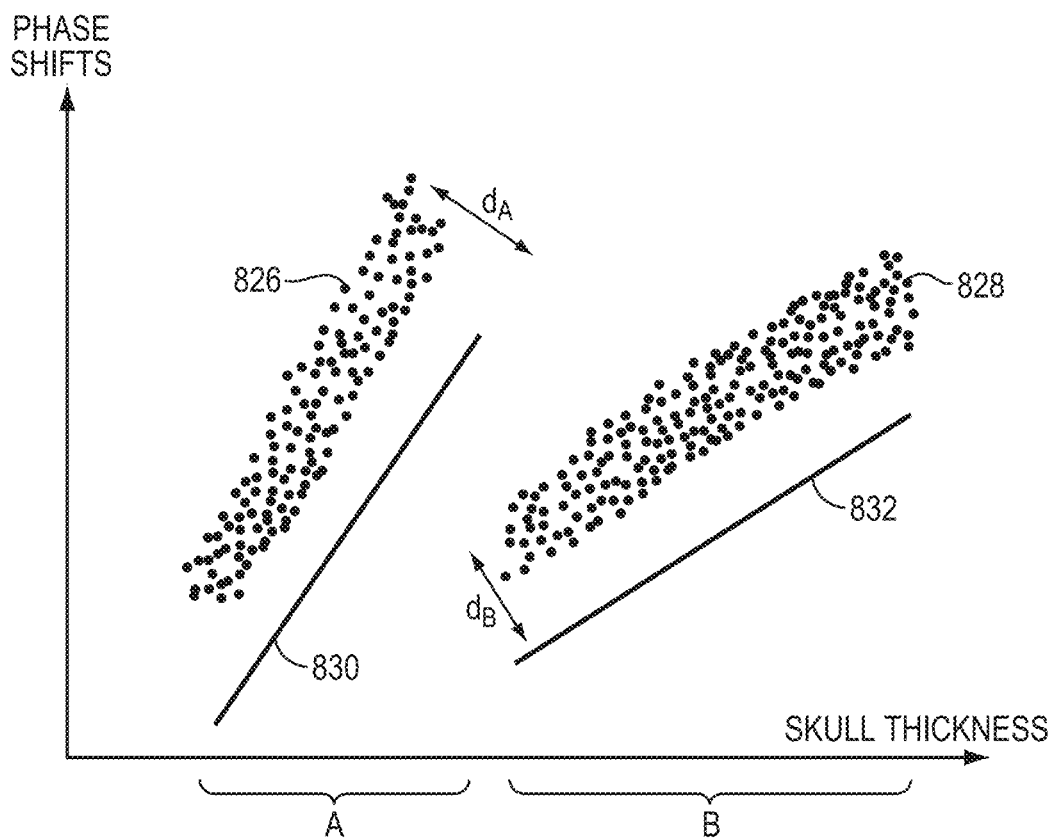

Referring to FIG. 8E, in some embodiments, the physical model first predicts the phase shifts 830, 832 of ultrasound waves when traversing skull regions A and B respectively (the predictions 830, 832 may be generated as linear fits on a cloud of points). A phase-bias difference, $d_A$, between the measured phase shifts 826 and the predicted phase shifts 830 can then be determined using the above-described correction approach. Similarly, a phase-bias difference, $d_B$, between the measured phase shifts 828 and predicted phase shifts 832 can be determined. The bias difference, d, between the data sets 826, 828 can be computed based on their differences $d_A$ and $d_B$ with respect to the physical model. In some embodiments, the data sets 826, 828 include measurements of ultrasound waves whose incidence angles onto the skull regions are below a threshold; this is because the physical model may give a more reliable prediction in this condition.

Figure 8F:
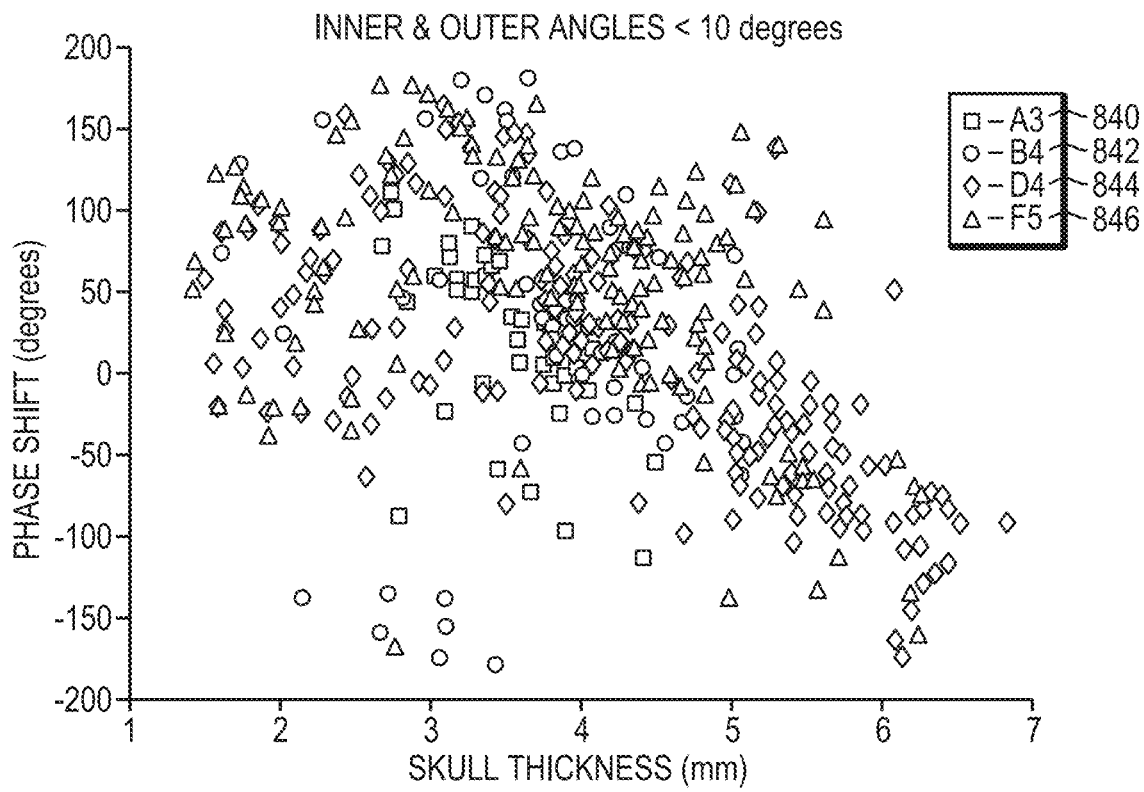

FIG. 8F depicts another regression result of a different skull. Again, the phase shifts generally negatively correlate to the skull thickness and data from the four skull measurements 840-846 collapses.

Phase-bias differences may also result from a difference between the planned and actual locations of the transducer elements 104 with respect to the hydrophone used to perform the measurements (with and without the skull) and from anatomical unknowns. Each element 104 has a different location; therefore, even though the acoustic beams emitted from different elements 104 may travel through the same medium to the target region (by plan) in the same measurement, the offset between the planned target and actual measurement location may result in an offset in the measured phases. In one implementation, the measurement location associated with each measurement is computationally, finely adjusted to the location found to minimize the error between the aberrations predicted using a physical model and the actual measured aberrations; the adjustment is applied to each of the transducer elements in each measurement according to its computed location as so to reduce the phase bias.

In addition, some or all data of the training set may be used to predict aberrations of the ultrasound beam when traversing the skull. In one embodiment, 1000 transducer elements 104 are activated in a single measurement; their receiving data is split into a training set that includes 900 elements and a test set that includes only 100 elements (e.g., selecting every $10^{th}$ element). In one embodiment, the test set may additionally or alternatively include data received in other measurement(s) and/or using other transducer elements. In one embodiment, the test set includes only measurements performed with skulls that are not used in any of the measurements in the training set. While multiple data sets may be acquired in multiple measurements, the skull patches used in the test set should not overlap with those used in the training set. In addition, the dataset may pass a verification test before being used in the learning process (for training, validation or test purposes). The verification test may include, for example, testing the functionality intactness of the transducer elements (e.g., based on the acoustic amplitude arriving the target in the filled liquid measurement), testing the correctness of the images (e.g., based on a thickness calculation in a predefined range) and/or limiting noise (e.g., based on the ratio of the acoustic amplitude arriving at the target in the presence of the skull to the acoustic amplitude at the target in the absence of the skull).

In order to use the model to predict the aberrations that will be exhibited by ultrasound waves when they traverse the skull of a new patient, it may be desired to consider the similarity between the new patient's skull and the skulls used to create the training set. In some embodiments, the similarity between two skulls is determined using images or imaging volumes acquired by the imager 112. For example, the imager 112 may acquire a series of images (e.g., CT images) of the new patient's skull. Based thereon, the skull patches through which the ultrasound waves travel prior to reaching a target region 306 can be identified and characterized. The topographies (e.g., thickness and orientation) of skull patches of the new patient may then be compared with those of the skull patches included in the training set to determine a metric of similarity. Typically, the comparison is performed on a pixel-by-pixel (or voxel-by-voxel if comparing the imaging volumes) basis. In some embodiments, the comparison is performed after the images are filtered, dimensionally reduced and/or processed using other approaches. The similarity metric may involve, for example, one or more of cross-correlation coefficients, the sum of squared intensity differences, mutual information (as the term is used in probability and information theory), ratio-image uniformity (i.e., the normalized standard deviation of the ratio of corresponding pixel values), the mean squared error, the sum of absolute differences, the sum of squared errors, the sum of absolute transformed differences (which uses a Hadamard or other frequency transform of the differences between corresponding pixels in the two images), or complex cross-correlation (for complex images, such as MRI images), and other techniques familiar to those of skill in the art in connection with image registration. Alternatively, the similarity between the two skulls may be determined based on the skull features associated with the images or image volumes and/or a combination thereof. Again, the features may include the skull's structure, shape, density, and/or thickness, the tilting angle between the skull patch and the acoustic beam path, the rotation angle of the skull patch, etc. The features may also include features extracted by algorithms, such as PCA, SIFT, autoencoders, etc.

In addition, various approaches may be utilized to improve prediction of the aberrations—i.e., reduce the deviation of the predicted value from the value measured using the sensor 310. For example, the imager 112 may be arranged based on the orientations of the transducer elements and other geometric characteristics, such as the target position and/or orientation of the relevant skull portion. In addition, the neural network may extract features associated with the skulls and assess the similarity between two skulls based on the extracted features. The skull features may also be extracted from various layers in the neural network. For example, when imaging intensities associated with the skull are used (e.g., using CT image intensities in Haunsfield units for an image slice taken within the skull along the skull orientation but not necessarily a uniform orientation), spatial invariance may be assumed, and the weights may be extracted from a fully connected layer that follows one or more convolutional layers with pooling. In some embodiments, a physical model is implemented to generate features associated with the skull, the measurement system, and/or the acoustic beams (e.g., a phase shift or an intensity at the target); the model-generated features, features extracted automatically from the neural network, and features related to online measurements (e.g., a phase and/or an amplitude of a reflected beam, a spectral activity, etc.) are then all included in the training set for similarity assessment and/or for data regression, classification or clustering process. In addition to the above-described similarity measures between two sets of features, a different similarity measure may be obtained between one set of features and multiple sets of features (e.g., features of cases in the training set). For example, if the similarity is performed in a feature-by-feature basis, to obtain a similarity measure per feature, a single, specific feature may be first compared to multiple features; the similarity measure of the specific feature may then be computed as a percentage of the cases in the multiple features whose similarity measures are above a predefined threshold corresponding to the specific feature.

It is possible to use the obtained similarity measures to estimate the correctness of a prediction. In one embodiment, a similarity criterion is used to determine how deviations from the skulls used in the training set affect the quality of the prediction; that is, predictions are performed on one or more test data sets using the trained model, and actual aberration measurements are performed on the target region formed by ultrasound beams passing through the skull or other target used for the test data set. The quality of the prediction is assessed by comparing the prediction to the actual measurements. By repeating this procedure with different test sets having different similarity measures relative to the skulls employed to train the model, the relationship between the similarity of a new skull to those used to train the model and the resulting effect on prediction accuracy can be estimated. In another embodiment, a similarity is assessed for the predicted case with cases that were not in the training set of the relevant predictor (e.g., cases that instead were in the validation and test sets). In some cases, predictor performance may be estimated based only on cases sufficiently similar to the new skull, i.e., where the similarity criterion does not fall below a predetermined threshold. For example, one embodiment uses the similarity to select a training set for the learning model (e.g., per treatment type or even per prediction case). Another embodiment uses a pre-trained learning model but fine tunes it to emphasize cases that are sufficiently similar to the new skull. Another approach uses the similarity measures combined with a learning model so that the estimated effect of similarity is refined as new data is acquired.

Figure 9A:
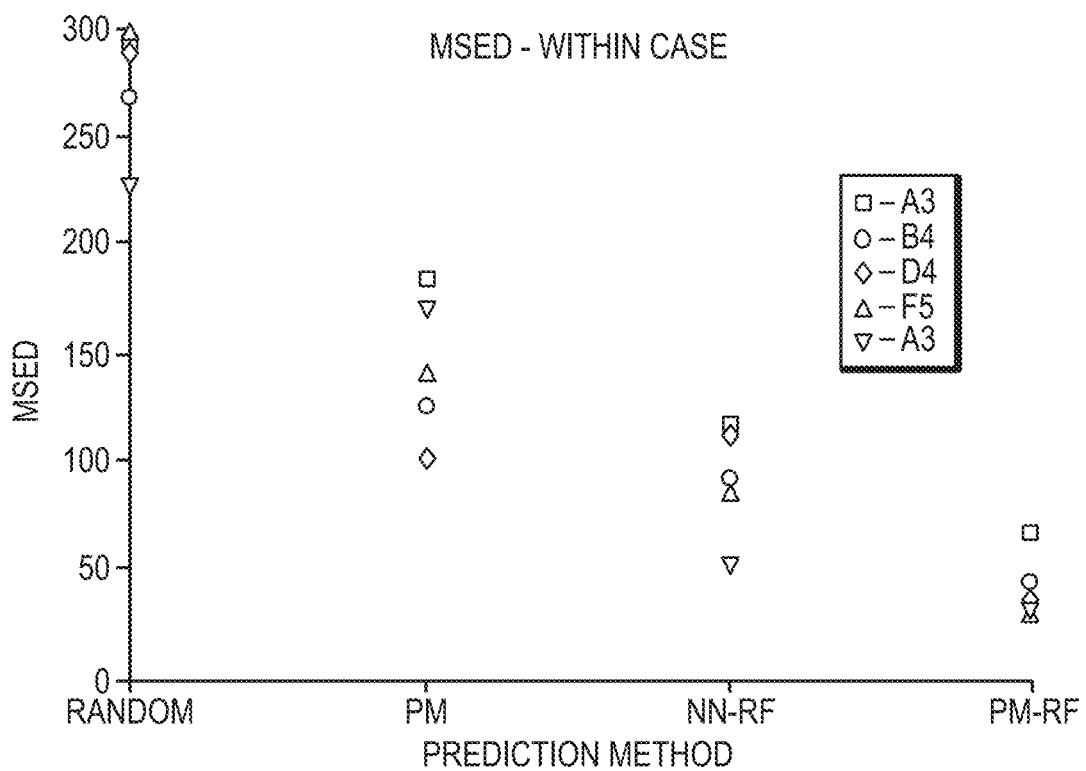
FIGS. 9A-9C depict various approaches for determining deviations of measured acoustic aberrations from predicted aberrations in accordance with various embodiments.
Figure 9B:
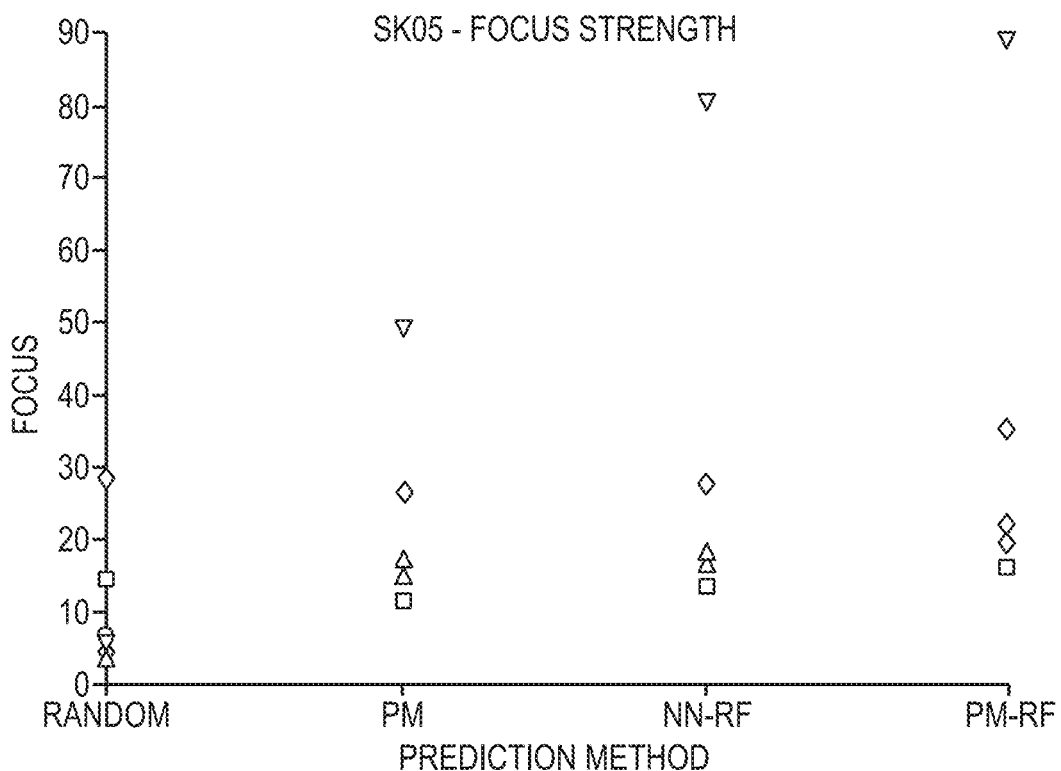
Figure 9C:
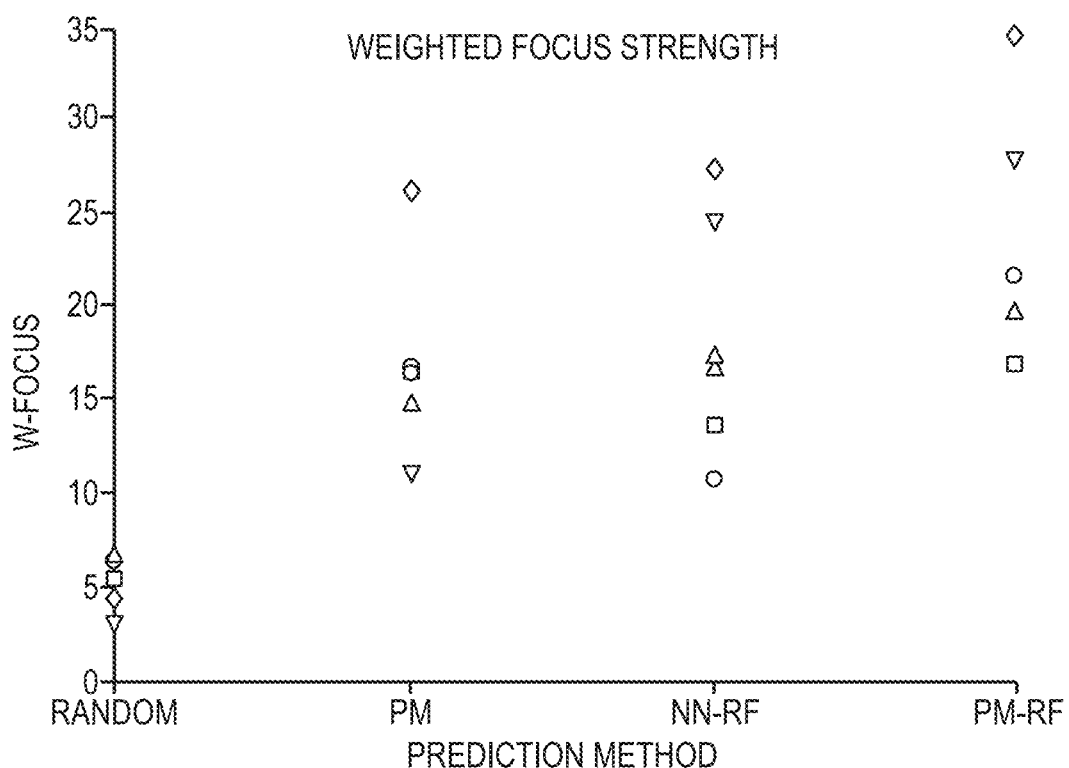

FIGS. 9A-9C depict deviations of the acoustic aberrations measured using the sensor 310 from the aberrations predicted using various approaches, such as a random phase shift selection (Random), a physical model (PM), a neural network together with a random-forest regression (NN-RF), and a physical model together with a random-forest regression (PM-RF). FIG. 9A depicts an assembled deviation, MSED, of the predicted phase shifts from the measured phase shifts. MSED is defined as:

$$MSED = \sum_{test\ element} |(Y_{predicted} - Y_{measured})^2|$$

where $Y_{predicted}$ and $Y_{measured}$ represent the predicted phase shift and measured phase shift (as angles in the range of $[-\pi, \pi]$), respectively, and test element represents the tested images/imaging volumes. FIG. 9B depicts an amplitude degradation, Focus, resulting from an error of the prediction. Focus is defined as:

$$Focus = \left| \sum_{test\ element} e^{i(Y_{predicted} - Y_{measured})} \right|$$

FIG. 9C depicts the degradation of the actual focal contribution resulting from a prediction error (which may depend on the amplitude degradation as well as the absolute transmission amplitude). The prediction may be performed using any approach as described above, and the error may be calculated based on the prediction and phases measured using the sensor 310. Wfocus is defined as:

$$WFocus = \left| \sum_{test\ element} \frac{A_{skull}}{A_{water}} e^{i(Y_{predicted} - Y_{measured})} \right|$$

where $A_{skull}$ and $A_{water}$ represent the measured amplitudes per element in the presence and absence of the skull, respectively. Wfocus may be a more realistic prediction criterion for the focus power as it mostly ignores errors in elements that do not contribute in practice to the focus. Besides being used as approaches for evaluating the prediction, each of the MSED, Focus and Wfocus may be used alone or modified by a scaling factor and/or a bias obtained from the tested data set to serve as a loss function in the learning model. In one implementation, the prediction result is evaluated using Pearson correlation. The above-described evaluations may be performed after manipulations of the predicted phases; the manipulations may include, for example, applying location adjustment relative to the measurements and/or fixing a phase-bias between the predictions and the measurements of the phase shifts.

Figure 10A:
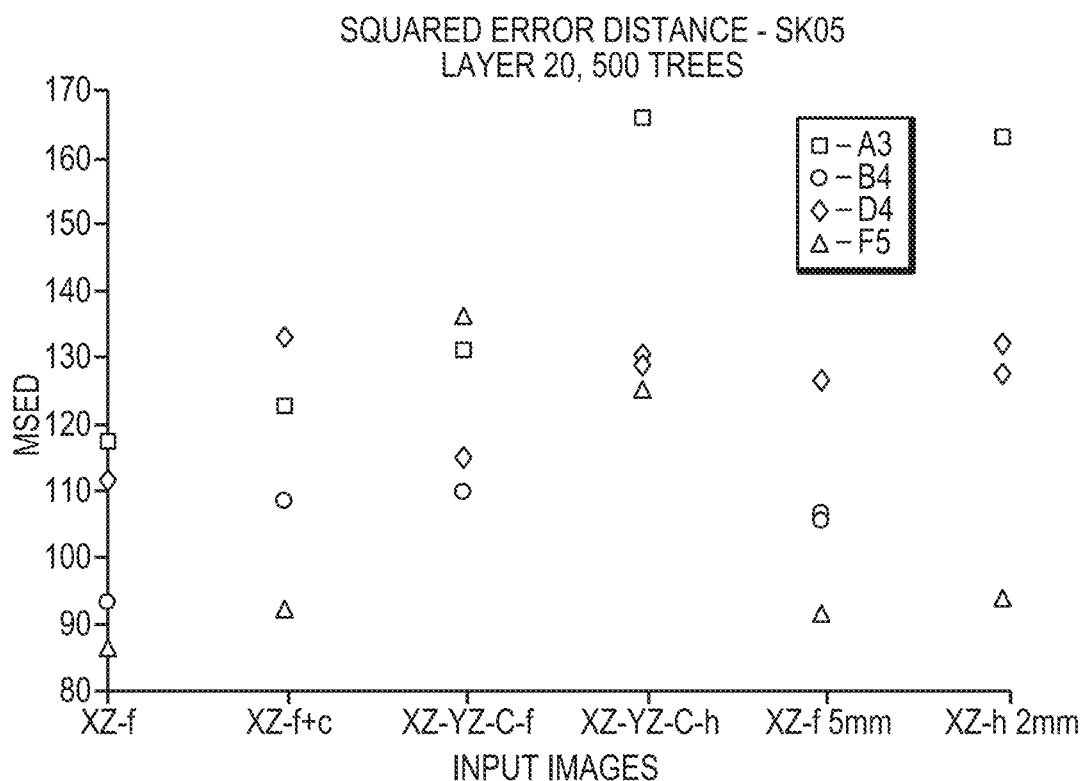
FIGS. 10A-10C depict the relationship between the degree to which predictions deviate from actual measurements and various types of input images utilized in a convolutional neural network in accordance with various embodiments.
Figure 10B:
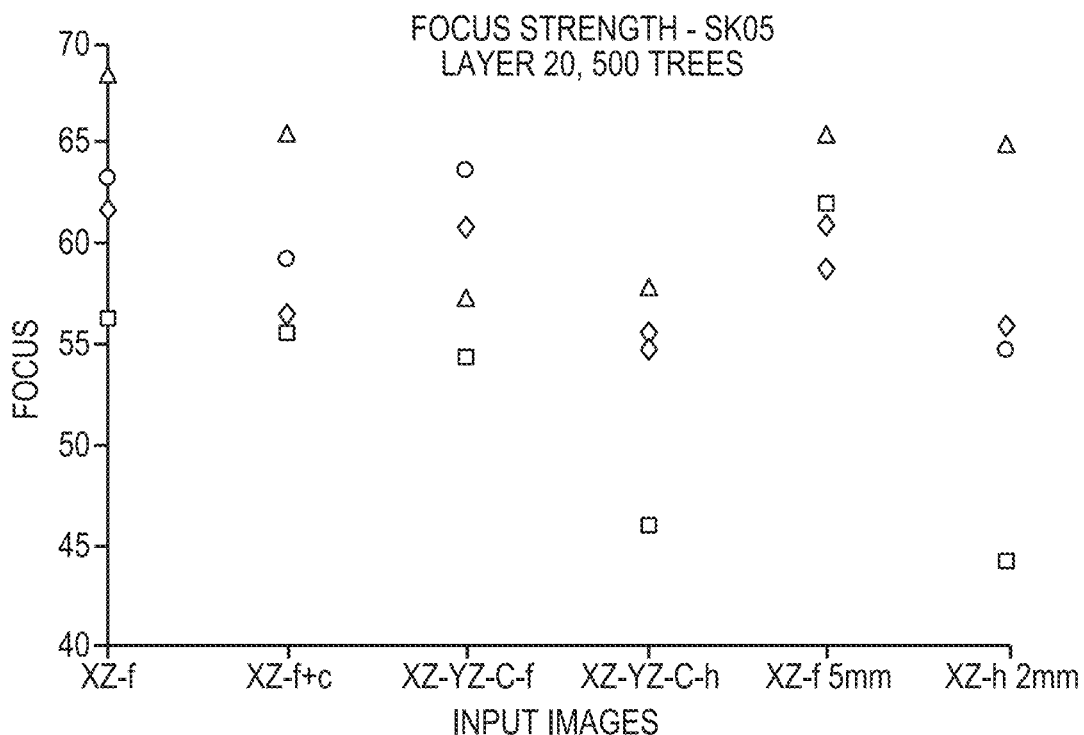
Figure 10C:
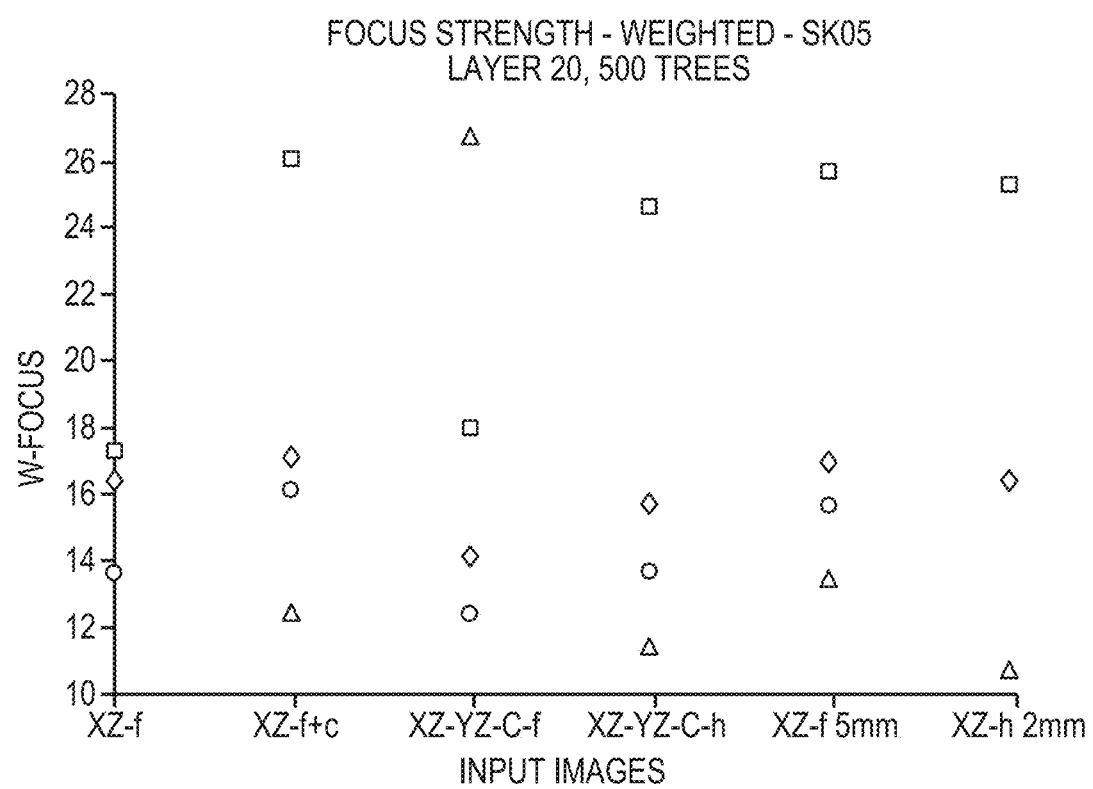
Figure 11A:
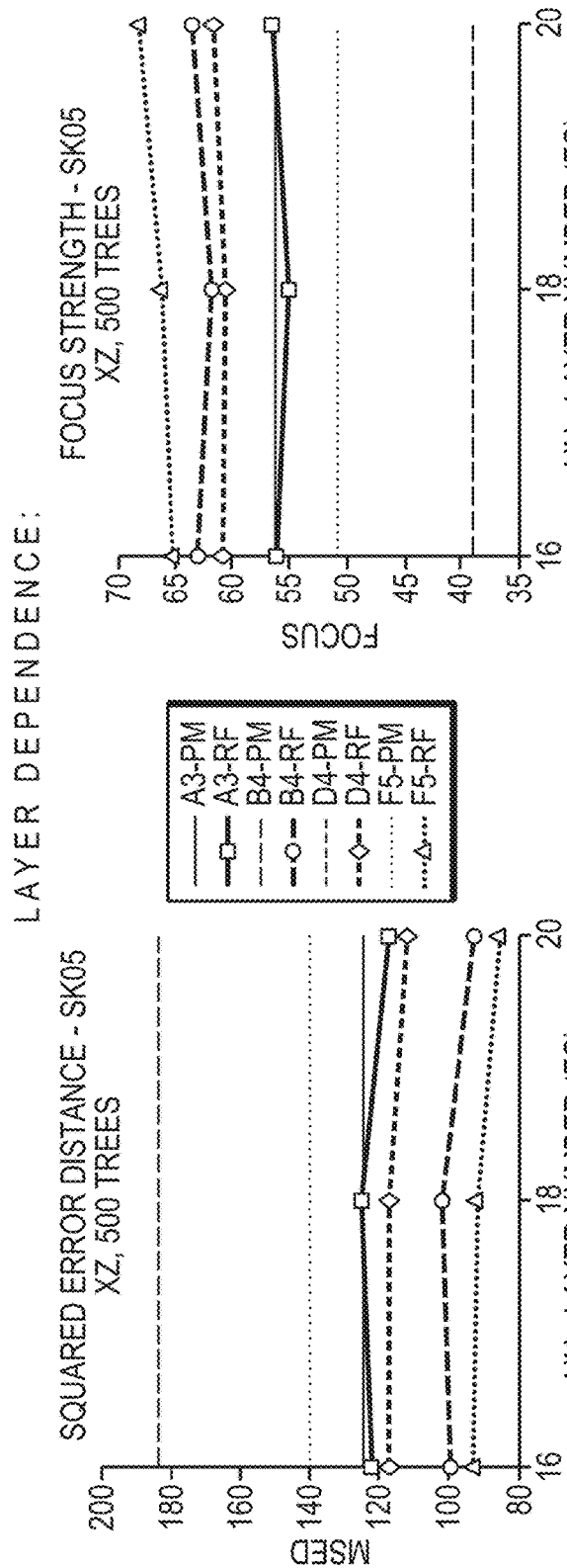
FIGS. 11A-11D depict the relationship between the degree to which predictions deviate from actual measurements and a layer number in a convolutional neural network having multiple layers (from which skull features are extracted and provided to a random-forest model) in accordance with various embodiments.
Figure 11B:
Figure 11C:
Figure 11D:
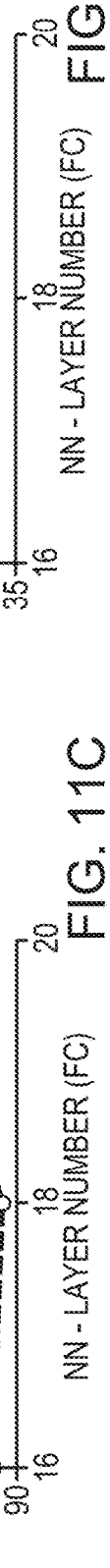

FIGS. 10A-10C depict the relationship between the deviations (including MSED, Focus, and Wfocus) and various types of input images for a convolutional neural network, where f denotes a full (and uniform) z range; h denotes a half z range, centered by the skull; +c represents the contrast difference between the images; XZ and YZ represent the slice directions; C represents a cylindrical slice along z; and 2 mm and 5 mm denotes a distance between consecutive slices).

A neural network that has been trained on a large amount of data and is ready to be used for prediction can also be used for feature extraction. Each layer is associated with different insights the neural network perceives from the input data. Therefore, when new data is provided to the network, the weights of the neurons in a particular layer provide an alternative representation of the data. If, for example, the network contains five layers, a new representation (i.e., features) of the input data can be extracted from each of the layers (except possibly the last layer, which provides the final result).

FIGS. 11A-11D illustrate this approach in practice, depicting the relationship between observed deviations (including MSED and Focus) and a layer number (which is fully connected) in the convolutional neural network (which has multiple layers) from which the features are extracted and used in a random forest model. FIGS. 12A-12F illustrate the relationship between the deviations (including MSED, Focus, and Wfocus) and the number of trees used in the random-forest model.

In general, functionality as described above, including, for example, analyzing the training set, performing machine-learning process, determining a relationship between the acoustic aberrations and tissue features and/or predicting aberrations resulting from the presence of new tissue features different from the features in the training set, whether integrated with the controller of the imager, and/or the ultrasound system, or provided by a separate external controller, may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

Certain embodiments of the present invention are described above. It is, however, expressly noted that the present invention is not limited to those embodiments; rather, additions and modifications to what is expressly described herein are also included within the scope of the invention. For example, imaging methods other than MRI may be used to track the locational tracker and anatomic region of interest.

What is claimed is:

1. An ultrasound system comprising:
   an ultrasound transducer comprising a plurality of transducer elements;
   a measuring system for acquiring a first series of measurements of a plurality of first anatomical regions through which the ultrasound waves emitted from the transducer elements will travel and a second series of measurements of a plurality of second anatomical regions through which the ultrasound waves emitted from the transducer elements have traveled, the second anatomical regions being different from the first anatomical regions; and
   a processor configured to:
   computationally train a predictor for predicting ultrasound aberrations based at least in part on the second series of measurements of the plurality of second anatomical regions;
   determine first values of a plurality of characteristics based at least in part on the first series of measurements of the plurality of first anatomical regions;
   execute the trained predictor using the first values as input to the trained predictor, whereby the predictor predicts, based on the first values, first aberrations of the ultrasound waves traveling through the first anatomical regions; and
   drive the transducer elements to compensate for the first aberrations.

2. The system of claim 1, wherein the processor is further configured to computationally predict a reliability of the predicted first aberrations.

3. The system of claim 1, wherein the measuring system comprising at least one of an imager for acquiring a first series of images of the first anatomical regions or an acoustic detector for detecting at least one of acoustic reflections from the first anatomical regions or acoustic spectral activities at the first anatomical regions.

4. The system of claim 3, wherein the imager comprises at least one of a magnetic resonance imaging device, a computer tomography device, a positron emission tomography device, a single-photon emission computed tomography device, or an ultrasonography device.

5. The system of claim 1, wherein the characteristics comprise at least one of anatomical characteristics, sonication parameters, information of the transducer elements, or characteristics of the measuring system.

6. The system of claim 5, wherein the sonication parameters comprises at least one of a frequency, an intensity or a phase associated with each one of the ultrasound waves.

7. The system of claim 5, wherein the information of the transducer elements comprises at least one of a size, a shape, a location or an orientation of each transducer element.

8. The system of claim 5, wherein the information of the transducer elements is extracted by at least one of transfer learning, autoencoding, principal component analysis or scale-invariant feature transform.

9. The system of claim 1, wherein the first aberrations comprise at least one of phase shifts, time delays, or changes in intensities associated with the transducer elements or shape distortion of a focus generated by the ultrasound waves.

10. The system of claim 1, wherein at least one of the first anatomical regions is traversed by a beam emitted by one of the transducer elements.

11. The system of claim 1, wherein the processor is further configured to (i) determine second values of the plurality of characteristics associated with the second anatomical regions based at least in part on the second series of measurements of the plurality of second anatomical regions and (ii) computationally train the predictor using the second values of the plurality of characteristics associated with the second anatomical regions and second ultrasound aberrations associated with the second values of the characteristics associated with the second anatomical regions.

12. The system of claim 11, wherein the processor is further configured to use the predictor to predict the first aberrations based at least in part on similarities between the first values of the characteristics associated with the first anatomical regions and the second values of the characteristics associated with the second anatomical regions.

13. The system of claim 12, wherein the similarity is determined based at least in part on pointwise similarity between the first and second series of the measurements.

14. The system of claim 12, wherein at least one of the values in the second values of the characteristics associated with the second anatomical regions is redundant.

15. The system of claim 14, wherein the second series of measurements comprise at least two redundant values corresponding to different second ultrasound aberrations.

16. The system of claim 14, wherein the second series of measurements comprise at least two redundant values corresponding to different preprocessing.

17. The system of claim 11, wherein the processor is further configured to predict the second values of the characteristics associated with the second anatomical regions using at least one of an aberration measurement or an aberration prediction.

18. The system of claim 11, wherein the predictor predicts the first aberrations based on a relationship between the second values of the characteristics associated with the second anatomical regions and the second ultrasound aberrations associated with the second values of the characteristics using a machine learning process.

19. The system of claim 18, wherein the relationship is determined using regression.

20. The system of claim 19, wherein the second ultrasound aberrations comprise phase shifts having real components and imaginary components, the regression being separately performed on the real and imaginary components.

21. The system of claim 18, wherein the relationship is determined using classification.

22. The system of claim 21, wherein the second ultrasound aberrations comprise phase shifts having real components and imaginary components, the classification being separately performed on the real and imaginary components.

23. The system of claim 11, wherein the processor is further configured to preprocess the second series of measurements of the second anatomical regions prior to determining the second values of the characteristics of the second anatomical regions.

24. The system of claim 23, wherein the processor is further configured to preprocess the first and second series of measurements in a plurality of steps, wherein at least one of the steps used to preprocess the first series of measurements is the same as one of the steps used to preprocess the second series of measurements.

25. The system of claim 23, wherein the second series of measurements comprise data derived from a first series of images of the second anatomical regions, and the preprocessing comprises determining rotation angles of the first series of images of the second anatomical regions prior to determining the second values of the characteristics of the second anatomical regions.

26. The system of claim 25, wherein the processor is further configured to acquire a second series of images of the second anatomical regions based at least in part on the determined rotation angles.

27. The system of claim 26, wherein the processor is further configured to acquire the second series of images of the second anatomical regions using resampling or interpolation of the second series of images of the second anatomical regions.

28. The system of claim 11, wherein the processor is further configured to preprocess the first series of measurements of the first anatomical regions prior to determining the first values of the characteristics of the first anatomical regions.

29. The system of claim 11, wherein the processor is further configured to remove bias in the second ultrasound aberrations.

30. The system of claim 11, wherein the processor is further configured to preprocess the second ultrasound aberrations based at least in part on estimation of a relative bias in the second ultrasound aberrations using a physical model.

31. The system of claim 30, wherein the processor is further configured to remove the relative bias in the second ultrasound aberrations.

32. The system of claim 11, wherein the processor is further configured to manipulate at least one aberration of the second ultrasound aberrations.

33. The system of claim 32, wherein the manipulation comprises at least one of unwrapping, scaling to a uniform ultrasound transmission frequency, or computational adjustment of a measurement location to a second measurement location.

34. The system of claim 1, wherein the predictor comprises a neural network.

35. The system of claim 1, wherein the processor is further configured to determine the plurality of characteristics of the first anatomical regions based at least in part on angles between orientations of the first anatomical regions and beam paths of ultrasound waves traveling therethrough.

36. The system of claim 1, wherein the characteristics comprise at least one of a structure, a shape, a density or a thickness of each of the first anatomical regions.

37. The system of claim 1, wherein the processor is further configured to determine accuracy of the predicted first aberrations of the ultrasound waves based on at least one of a reliability estimation of the prediction, a similarity measure between the first series and the second series of measurements, or a prediction success associated with the second series of measurements.

38. An ultrasound system comprising:
 an ultrasound transducer comprising a plurality of transducer elements;
 a measuring system for acquiring a first series of measurements of a plurality of first anatomical regions through which the ultrasound waves emitted from the transducer elements will travel and a second series of measurements of a plurality of second anatomical regions through which the ultrasound waves emitted from the transducer elements have traveled, the second anatomical regions being different from the first anatomical regions; and
 a processor configured to:
  computationally train a predictor for predicting an ultrasound intensity at a target region based at least in part on the second series of measurements of the plurality of second anatomical regions;
  determine first values of a plurality of characteristics based at least in part on the first series of measurements of the plurality of first anatomical regions;
  execute the trained predictor, using the first values as input to the trained predictor,
  whereby the predictor predicts, based on the first values, a first ultrasound intensity of the ultrasound waves at the target region after traveling through the first anatomical regions; and
  drive the transducer elements to generate a desired ultrasound focus at the target region.

39. The system of claim 38, wherein the measuring system comprises an imager comprising at least one of a magnetic resonance imaging device, a computer tomography device, a positron emission tomography device, a single-photon emission computed tomography device, or an ultrasonography device.

* * * * *